United States Patent
Heumann et al.

(10) Patent No.: US 7,108,424 B2
(45) Date of Patent: Sep. 19, 2006

(54) METHOD AND APPARATUS FOR CALIBRATION OF INDIRECT MEASUREMENT SYSTEMS

(75) Inventors: John M. Heumann, Loveland, CO (US); Eduardo Acosta, Ann Arbor, MI (US)

(73) Assignee: Agilent Technologies, Inc., Palo Alto, CA (US)

(*) Notice: Subject to any disclaimer, the term of this patent is extended or adjusted under 35 U.S.C. 154(b) by 64 days.

(21) Appl. No.: 10/797,993

(22) Filed: Mar. 11, 2004

(65) Prior Publication Data

US 2005/0201524 A1 Sep. 15, 2005

(51) Int. Cl.
G01D 18/00 (2006.01)
G01N 23/06 (2006.01)

(52) U.S. Cl. .................. 378/207; 378/56; 250/252.1

(58) Field of Classification Search ............ 378/51–58, 378/207, 19, 98.8; 73/1.79, 1.81; 250/252.1, 250/370.09

See application file for complete search history.

(56) References Cited

U.S. PATENT DOCUMENTS

| 4,472,823 | A | * | 9/1984 | Waltham | 378/19 |
|---|---|---|---|---|---|
| 6,148,057 | A | * | 11/2000 | Urchuk et al. | 378/18 |
| 6,201,850 | B1 | * | 3/2001 | Heumann | 378/56 |
| 6,347,131 | B1 | * | 2/2002 | Gusterson | 378/54 |
| 6,848,827 | B1 | * | 2/2005 | Wu et al. | 378/207 |
| 2002/0095087 | A1 | * | 7/2002 | Mourad et al. | 600/442 |

OTHER PUBLICATIONS

George W. Snedecor and William G. Cochran. Statistical Methods, eighth edition (Ames, Iowa: Iowa State University Press, 1989), p. 398-419.*

* cited by examiner

Primary Examiner—Allen C. Ho

(57) ABSTRACT

A calibration technique is presented for calibrating non-reference indirect measurement systems with respect to a reference indirect measurement system. A reference map function fitting procedure fits a reference map function based on known values of a parameter of interest associated with reference calibration samples and corresponding reference values associated with the reference calibration samples. A correction function fitting procedure fits a correction function based on reference values for calibration samples measured on or simulated for the reference indirect measurement system and corresponding values measured on the non-reference indirect measurement system. During normal use, the non-reference indirect measurement system obtains measurements, corrects the measurements using the correction function, and estimates the parameter of interest of the object of interest using the reference map function based on the corrected measurements.

43 Claims, 14 Drawing Sheets

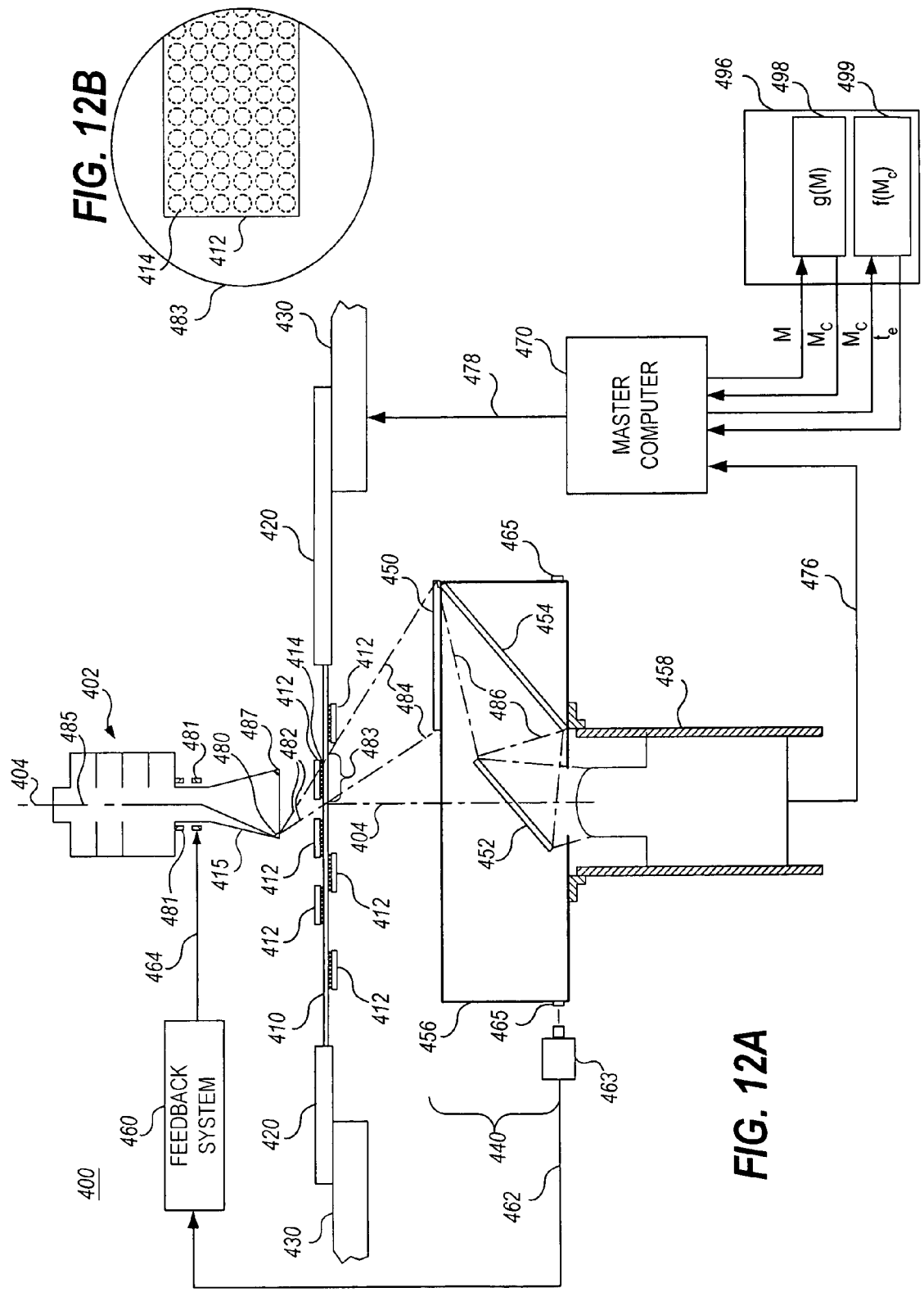

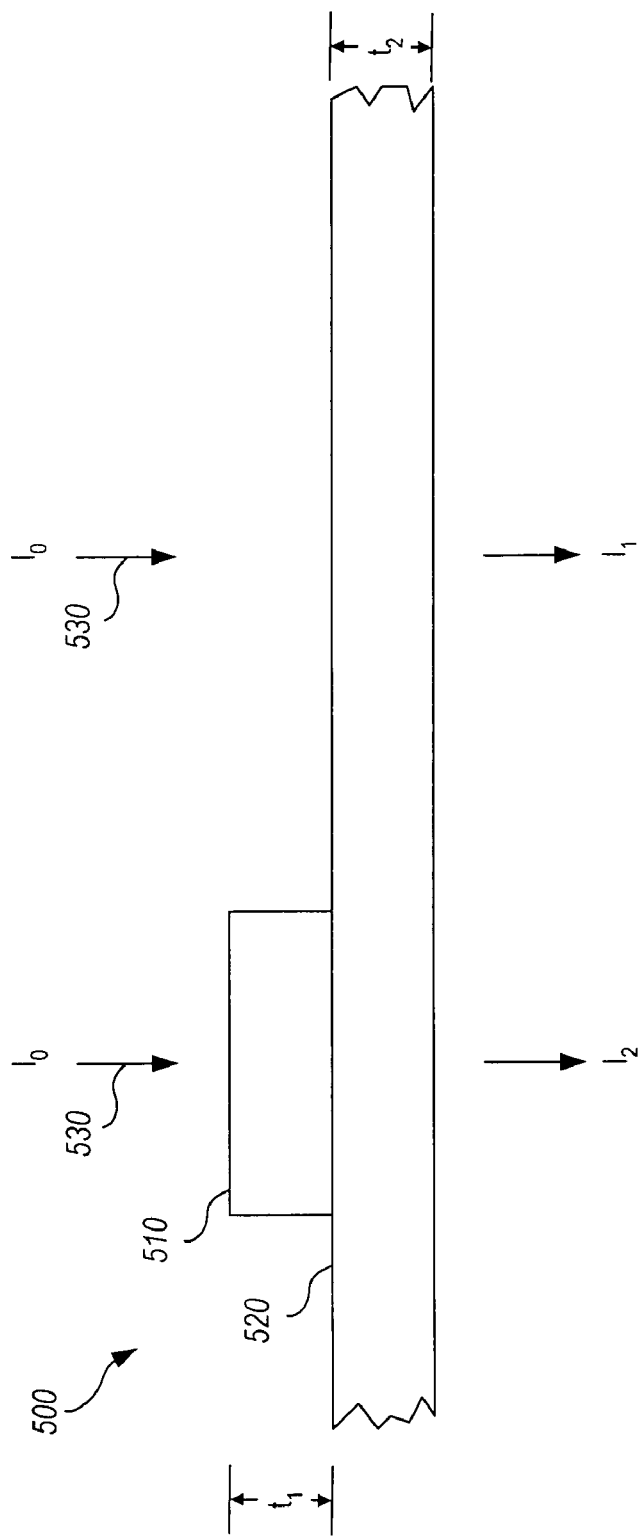

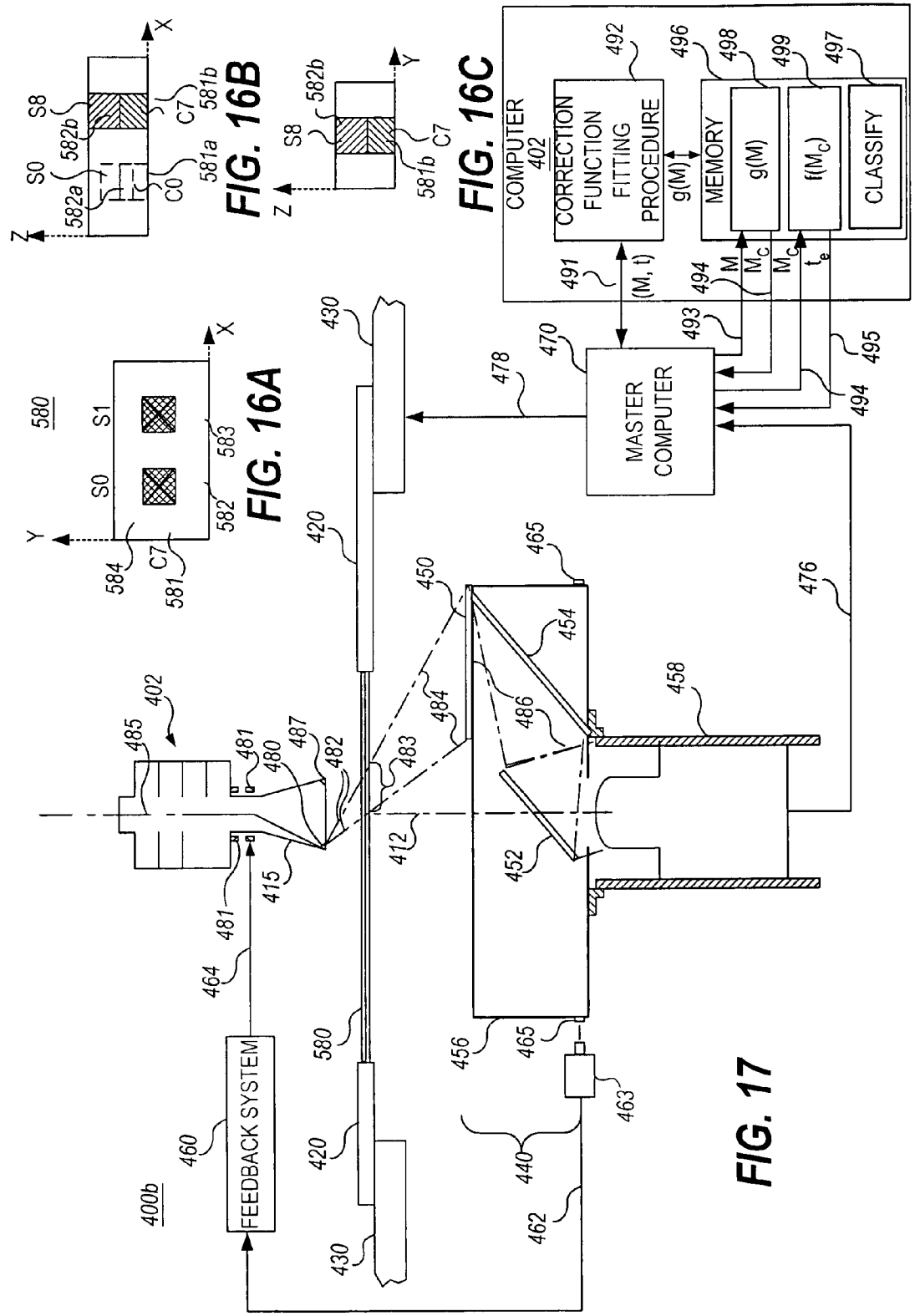

METHOD AND APPARATUS FOR CALIBRATION OF INDIRECT MEASUREMENT SYSTEMS

BACKGROUND OF THE INVENTION

The present invention relates generally to instrument calibration and more particularly to a novel method and apparatus for calibration of indirect measurement and inspection systems.

Inspection and measurement systems often depend on accurately sensing one or more physical parameters reflecting a process of interest. In electronics, for example, automated test equipment (ATE) may, in various situations, be required to accurately measure voltage, current, resistance, or phase. In radiation dosimetry, systems may be required to accurately measure total accumulated dose or radiation level. Similarly, systems may be required to measure length, time, mass, or any of a variety of physical parameters. It is generally desirable that the measured result be repeatable, portable, and accurate. Repeatability means that multiple consecutive readings of the same parameter on a single system give the same result within the required tolerance. Repeatability is primarily a function of system design and is beyond the scope of the present invention. Portability means that comparable results should be obtained if the same measurement is taken using different instances of the same system (i.e., two voltmeters of the same model should return similar or identical results when performing the same measurement). Accuracy means that the measured results should be a true reflection of the underlying process, without the introduction of bias. Since all measurement and inspection systems are subject, in varying degree, to manufacturing variations and drift, periodic calibrations of the measurement system are typically required to assure portability and accuracy.

Frequently, calibration involves adjusting the system to obtain a correct reading on one or more known calibration samples. It is desirable and often required, for the calibration samples to be traceable to a primary standard maintained by a widely recognized agency. In the United States, for example, the National Institute of Standards and Technology (NIST) typically maintains primary calibration standards. Depending on the economics of a particular situation, calibration samples may be shipped with the system or may be incorporated into the system itself. More commonly, however, small systems are returned to centralized metrology labs for periodic calibration, while for larger systems it may be necessary to transport the standards to the system. Such approaches are widely used and often suffice when the physical property of interest is directly sensed by the system in question, or when the relationship between the quantity sensed and the physical property of interest is well known. (An accurate voltage sensor can be combined with a known resistance to provide a current sensor, for example).

In many cases, however, inspection and measurement systems must rely on measurements that only indirectly reflect the physical parameters of interest. The Agilent 5DX Automated X-ray Inspection (AXI) System manufactured by Agilent Technologies Inc. of Palo Alto, Calif., for example, uses penetrating radiation, specifically x-rays, to form cross-sectional images of solder joints in electronic assemblies, and to automatically identify defective and/or unreliable joints. A key physical parameter for such identification is solder thickness. Unfortunately, the relationship between solder thickness and the gray value observed in cross-sectional or transmission images is complex and difficult to model accurately. While thicker joints typically appear darker, all other factors being equal, the relationship is complicated by several factors. Due to scatter, the gray value observed for a particular joint can be affected by neighboring or even distant portions of the assembly. Additional problems arise from the use of broadband (typically bremsstrahlung) x-ray sources in conjunction with monochromatic detectors. When the object under inspection comprises multiple materials, each material has an x-ray attenuation coefficient that depends on energy in a characteristic way. Monochromatic detectors sense only the integrated intensity reaching the detector, so it is typically not possible to unambiguously recover the thickness of the intervening materials. Similar problems are well known in other areas, for example, in various forms of quantitative medical imaging including, but not limited to, computed tomography (CT), positron emission tomography (PET), and single photon positron emission computed tomography (SPECT).

Calibration in such indirect-sensing systems is often expensive, time-consuming, and error prone. A calibration coupon, for example, comprising differing known values of a parameter of interest may be provided with each indirect-sensing system to be used as a set of calibration samples. For calibration, measurements are taken of an indirect parameter under standard conditions, and a fitting procedure generates a mathematical model describing the non-linear relation between the measured indirect parameter value and the actual parameter of interest. The fitting procedure must be repeated periodically to compensate for drift of known and unknown origin.

As a specific example, consider automated X-ray inspection systems such as the Agilent 5DX AXI System mentioned previously. Using the prior art technique, each 5DX system site is provided with a thickness coupon containing eight copper strips of varying thickness (including a thickness of zero) which intersect nine solder strips of varying thickness (including a thickness of zero), for a total of seventy-two "representative" calibration samples. During calibration, the gray values of each intersection point are measured under standard conditions, and a fitting procedure, such as one described in U.S. Pat. No. 6,201,850 (hereby incorporated by reference for all that it teaches) to Heumann and owned by the present assignee of interest, constructs a mathematical model describing the non-linear relation between measured gray values and corresponding solder thicknesses.

A number of disadvantages, representative of indirect measuring systems, are apparent in the above example. A large number of calibration samples may be required, resulting in large expenses. Additionally, measuring many samples accurately is time consuming, reducing system availability for normal use. Fabrication of the calibration samples can pose its own challenges. In the case of a thickness coupon, described above, eutectic solder is soft and easily deformed. As a result, strips whose thickness is controlled to the desired accuracy are not readily available commercially. This necessitates measuring the thickness of each solder strip using a NIST traceable instrument. However, mechanical measurement can alter solder strip thickness. Thickness may therefore not be known precisely, and may vary within a coupon or from coupon to coupon. Thickness measurements may suffer from portability and accuracy problems as a result. Finally, the need to minimize the time that the system is unavailable for production use limits the sophistication of the fitting procedure used to describe the relationship between measured gray values and solder thickness.

Accordingly, a calibration technique for indirect measurement and inspection systems is needed that avoids the aforementioned problems, yet is economical, automated, fast, highly repeatable, portable, and accurate.

SUMMARY OF THE INVENTION

The present invention is a novel calibration technique for indirect measurement and inspection systems that solves the aforementioned problems of the prior art.

In accordance with the invention, a reference indirect measurement system is calibrated based on a plurality of reference calibration samples having differing known values of the physical parameter of interest, for example using a superset calibration test coupon. Reference values for the reference calibration samples are obtained either by taking measurements on the reference indirect measurement system, or by simulation. A reference map function fitting procedure constructs a reference map function, $f(M_C)$, describing the (typically non-linear) relationship between reference values and corresponding known parameter values. The reference map function fitting procedure need only be performed a little as one time on a single reference system. The resulting reference map function, $f(M_C)$, is provided to each instance of one or more non-reference indirect measurement systems.

Each one or more non-reference indirect measurement systems are also provided with a correction function fitting procedure that generates a correction function, $g(M)$, that corrects any measurement, M, to its corrected value $M_C$ to minimize differences between the local system and the reference system. In particular, the correction function fitting procedure obtains measurement values from a small number of calibration samples measured on the particular non-reference indirect measurement system. The correction function fitting procedure fits these obtained measurement values to corresponding known reference values that are associated with each of the calibration samples and are measured on or simulated for the reference indirect measurement system to generate a correction function. Preferably, the correction function fitting procedure fits the calibration sample points to a line/linear function, a low order polynomial, or other parametric function characterized by a small number of parameters to generate the correction function, $g(M)$. Non-reference indirect measurement systems may then be corrected quickly and accurately to match the results that would have been obtained had the reference indirect measurement system made the same measurements, thereby generating a high degree of portability and accuracy.

In summary, reference map function, $f(M_C)$, is generated once (or a small number of times) for a single reference system and is preferably used by all other such systems. Generation of correction function, $g(M)$, on the other hand, is performed periodically or as needed on each local system to correct any measurement differences due to system drift, change in environment, etc.

During normal operation, a given indirect measurement system recovers a raw measurement value, M, applies the local correction function, $g(M)$, to generate a corrected measurement value, $M_C$, and applies the global reference map function, $f(M_C)$, to generate an estimate of the physical parameter of interest for that object of interest. The object/parameter of interest may then be classified into one of a plurality of classes based on the estimated value of the physical parameter for the object of interest.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein:

FIG. 12A is a schematic diagram of a typical laminographic apparatus in which the present invention may be employed;

FIG. 12B is a top view enlargement of an inspection region shown in FIG. 12A;

FIG. 13 is a schematic cross sectional representation of a portion of a two component assembly that may be inspected by the laminographic apparatus of FIG. 12A;

FIG. 16A is a top view (in the x-y dimension) of a two-point subset calibration test coupon used for performing correction function calibration of a local laminographic apparatus to generate a correction function g(M);

FIG. 16B is a side view (in the x-z dimension) of the two-point subset calibration test coupon of FIG. 16A;

FIG. 16C is a side view (in the y-z dimension) of the two-point subset calibration test coupon of FIGS. 16A and 16B;

FIG. 17 is a schematic diagram of a local laminographic apparatus in which the subset test calibration coupon of FIGS. 14A–14C is under inspection in order to calibrate the local laminographic apparatus to the reference laminographic apparatus of FIG. 15.

DETAILED DESCRIPTION

Figure 1:
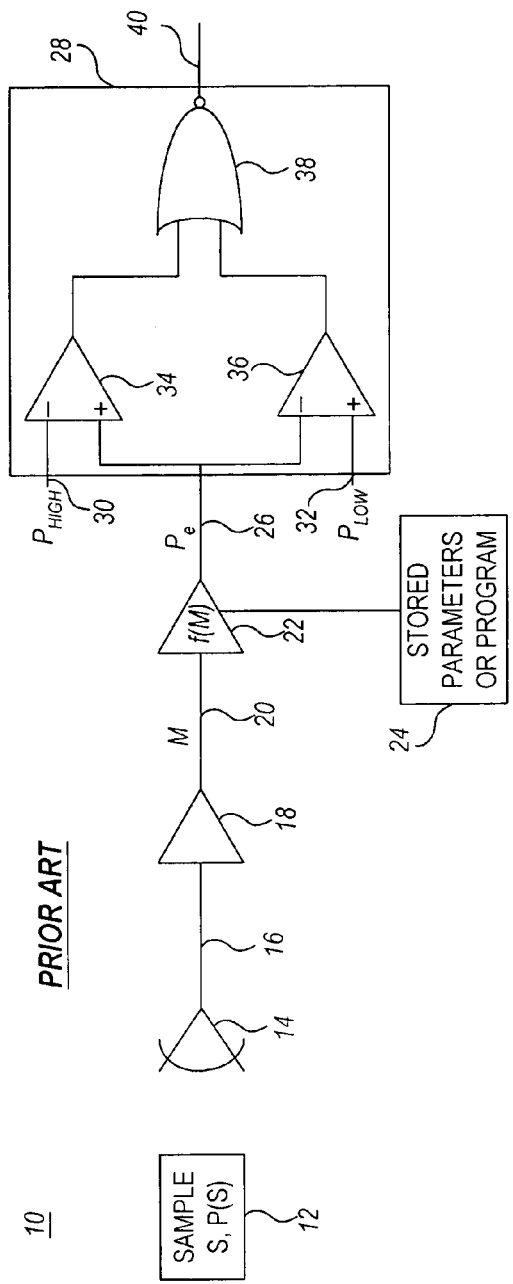
FIG. 1 is a schematic block diagram of a first embodiment of a prior art indirect measurement system.

Turning now to the drawings, FIG. 1 is a simplified schematic block diagram of a first embodiment of a prior art indirect measurement system 10. As illustrated, system 10 includes one or more sensors 14 which generate a sensed signal 16 that feeds a buffer/amplifier 18. The output 20 of the buffer/amplifier 18 is input to a map function 22. The map function 22 may be implemented as program instructions stored in memory 24 and executed by a processor (not shown). The map function 22 may be algorithmic, actively calculating an estimated parameter value, $P_e$, for each measurement value, M, or alternatively, estimated parameter values for given measurement values may be stored in memory, for example in a look-up table. The parameters and/or algorithms which need to be stored can reside in computer memory, in analog hardware (e.g. in settings of potentiometers or choice of component values), or in algorithmic form (e.g. executable code residing in firmware or software. The output 26 of the map function 22 is connected to a classifier circuit 28 implemented in the illustrative embodiment by a first comparator 34, a second comparator 36, and a NOR gate 38.

In operation, a sample 12, S, possessing a physical property, P(S), of interest is observed via the one or more sensors 14. The sensed result 16 is conditioned/amplified by the buffer/amplifier 18 to generate one or more measurements 20, M. The measurement 20, M, is reflective of the physical property or properties, P(S), of the sample 12, S, but as described above, the relation may be complex and poorly understood. A stored function, f(M), approximating this relation gives an estimate 26, $P_e$, of the physical parameter of interest. If desired, the estimated value 26, $P_e$, of the physical parameter of interest is then passed to classifier 28 for determination of whether to pass or fail the sample 12 under inspection. In simple cases, for example, classification may be performed, as illustrated, by comparing the estimated value 26 to one or both of low and high limits, 32 $P_{LOW}$, and 30 $P_{HIGH}$, respectively. If the map function 22, f(M), is monotonic and single-valued (i.e., $f^{-1}$(M) exists and is unique), the measurement 20, M, can be compared directly to limits $M_{LOW}=f^{-1}(P_{LOW})$ and $M_{HIGH}=f^{-1}(P_{HIGH})$, for example. It will be understood by those skilled in the art that this description should be interpreted conceptually rather than literally, and that many equivalent implementations are possible.

Figure 2:
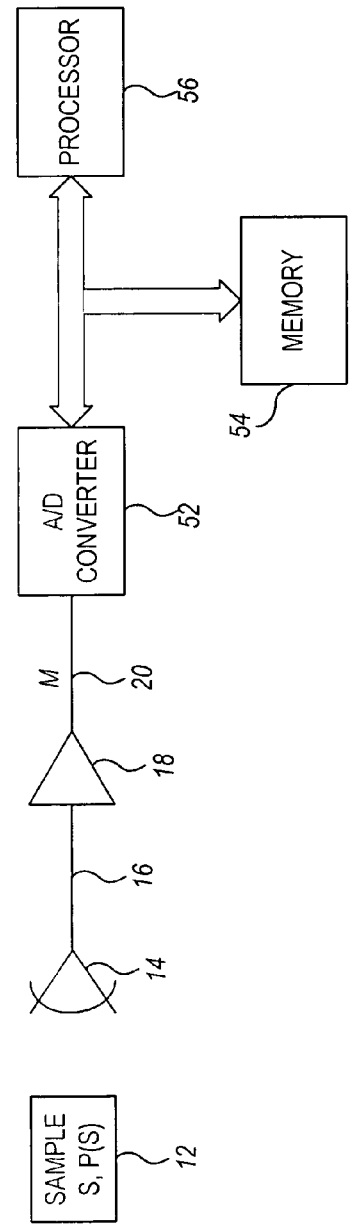
FIG. 2 is a schematic block diagram of a second embodiment of a prior art indirect measurement system.

Similarly, the measurement 20, M, may be digitized and some or all subsequent operations performed digitally rather than in analog circuitry, as illustrated in the system 50 in FIG. 2, which shows a second embodiment of a prior art indirect measurement system. Analog-to-digital (A/D) converter 52 converts the analog measurement 20, M, to a digital signal, which is processed by a digital map function under the control of a processor 56. In this embodiment, the map function, f(M), is stored in memory 54 along with any other algorithms and data required for system operation.

Figure 3:
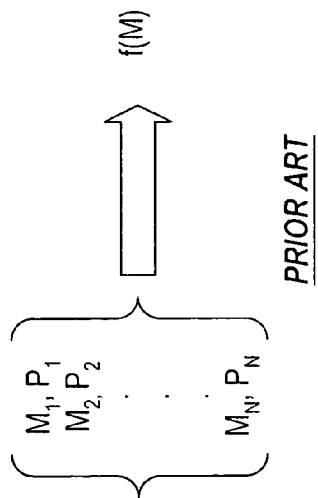
FIG. 3 is a diagram illustrating prior art generation of a reference map function from a set of pairs of measured sample values and corresponding parameter values.

As described above, indirect measurement systems have conventionally been calibrated by measuring a large number, N, of calibration samples, $\{S_i\}$ at points, $\{M_i, P_i\}$, where i=1, . . . N, which are used to construct a new estimate of f(M), or to improve an existing estimate, as illustrated schematically in FIG. 3. Here $M_i$ denotes the measurement obtained for the $i^{th}$ sample, $S_i$, having known value, $P_i$, of the physical parameter of interest.

Typically, f(M) will be chosen so that $f(M_i) \approx P_i$, in addition to satisfying certain regularity constraints. It is often desirable for f(M) to be monotonic and easily invertible. Fitting methods, i.e., methods for estimating or approximating f(M), are well-known, such as described in U.S. Pat. No. 6,201,850, cited in the background section, and are beyond the scope of the present invention. The process of: a) measuring a set of calibration samples, and b) constructing or revising an estimate of f(M) will be referred to hereafter as "conventional calibration".

Within constraints dictated by economics of their marketplace, manufacturers typically strive to make measurement and inspection systems as identical as practical. Typically, they are relatively successful in this regard. As a result differences in the directly sensed quantities between any two systems of the same type are generally small, although not insignificant. They may have complex and poorly understood origins, but they will generally not be large. By exploiting this property, the present invention constructs a two-stage calibration method for indirect measurement systems that avoids many of the drawbacks of the conventional approach.

In both direct and indirect measurement systems, the difference between the directly measured quantities on two such systems can be typically modeled with good accuracy as a low order polynomial. This approach is applicable independent of the cause of the discrepancies, so long as the differences are small and smoothly varying. Consider, for example, the response of two imaging systems to a set of samples. Let the values measured on the first system be $I_1(j)$ and that of the second system to be $I_2(j)$, where j denotes sample number. The error or discrepancy between measured values on the two systems may be denoted by $\delta(j)=I_2(j)-I_1(j)$. Assuming that indices j are ordered such that the $I_1(j)$ are monotonic, $I_2$ and $\delta$ can be equally well expressed as a function of $I_1$, for example, rather than of j, e.g., $I_2(I_1(j))$ and $\delta((I_1(j))$. Because the discrepancy between systems is small, the unknown functional dependence can be expanded in power series, e.g.:

$$\delta(I_1) = a_0 + a_1 I_1 + a_2 I_1^2 + \ldots$$

The well-known Taylor series, for example, has coefficients $$a_0 = \delta(I_1 = 0)$$

$$a_1 = d\delta/dI_1 (I_1 = 0)$$

$$a_2 = 0.5 d^2\delta/dI_1^2 (I_1 = 0) \ldots$$

When the discrepancy between systems is sufficiently small and the functional dependence sufficiently well behaved, δ can be accurately approximated using only the first two terms in the power-series expansion (i.e., by a straight line). In this case, a simple two-point calibration (i.e., measuring $I_1$ and $I_2$ at two values of j, preferably corresponding to well separated values of $I_1$ suffices to correct measured values on a local system to match those on a reference system. Additional data points, if available can be used to assign confidence intervals to the fitted parameters.

The present invention utilizes the calibration correction technique just described and applies it to indirect measurement systems to correct a each measurement M prior to estimating the physical parameter of interest using a reference map function $f(M_C)$.

Figure 4:
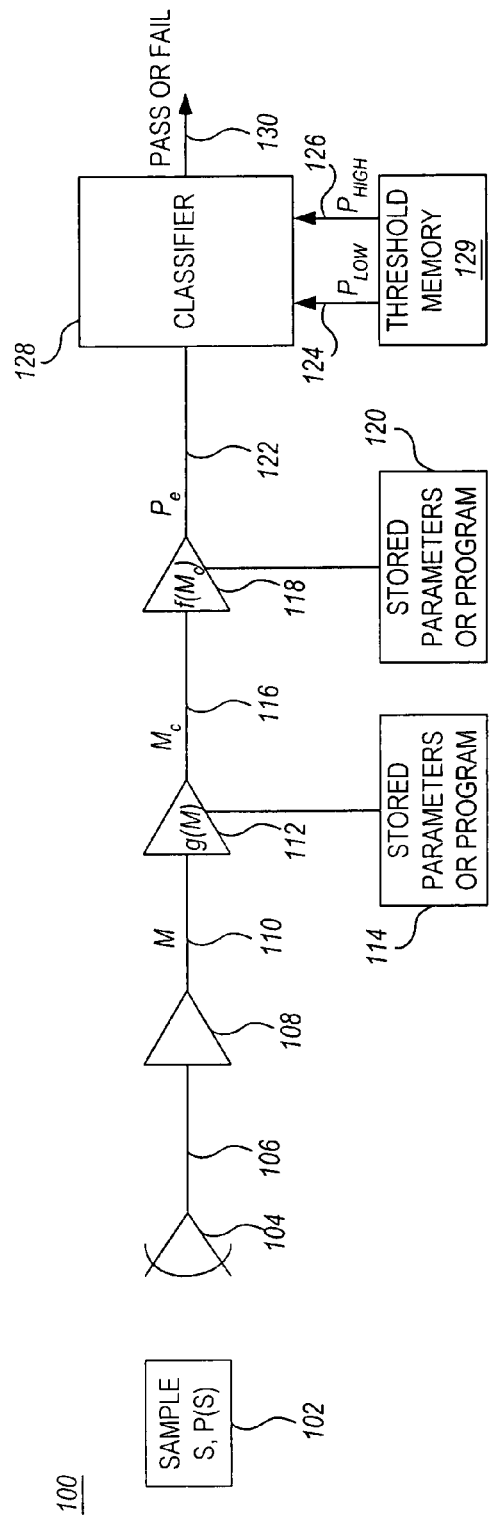
FIG. 4 is a schematic block diagram of an indirect measurement system implemented in accordance with the invention.

FIG. 4 is a schematic block diagram illustrating an improved indirect measurement system 100 implemented in accordance with the invention. As illustrated, system 100 includes one or more sensors 104 which generate a sensed signal 106 that feeds a buffer/amplifier 108. The output 110 of the buffer/amplifier 108 is input to a correction function 112, g(M), which may access a memory 114 which stores correction parameters or program code. The parameters and/or algorithms can reside in computer memory, in analog hardware (e.g. in settings of potentiometers or choice of component values), or in algorithmic form (e.g. executable code residing in firmware or software). The output of the correction function 112 is input to reference map function 118, $f(M_C)$, which may access parameters or programs stored in memory 120. The output 122 of the reference map function 118 is, optionally, input to classifier 128. The classifier 128 may access a memory 129 that stores one or more classification thresholds (e.g., a high limit 126, $P_{HIGH}$, and a low limit 124, $P_{LOW}$) for use in determining in which of a plurality of classes an object belongs based on the estimated parameter value of the object of interest. For simplicity, the details of the classifier 128 have been omitted. As before, this model is to be interpreted conceptually rather than literally, and many functionally equivalent implementations are possible. Many operations can be performed in either analog or digital fashion, for example.

In operation, a sample 102, S, possessing a physical property, P(S), of interest is observed via the one or more sensors 104. The sensed result 106 is conditioned/amplified by the buffer/amplifier 108 to generate one or more measurements 110, M.

The present invention applies the correction function 112, g(M), to each measurement M 110 resulting in a corrected measurement 116, $M_C$. Correction function 112, g(M), minimizes the small discrepancies between systems. Corrected measurement 116, $M_C$, is reflective of the physical property, P(S), of the sample 102, S, but as described above, the relation may be complex and poorly understood. The reference map function 118, $f(M_C)$, processes the corrected measurement 116, $M_C$, approximating this relation to generate an estimate 122, $P_e$, of the physical parameter of interest. If desired, the estimated value 122, $P_e$, of the physical parameter of interest is used by classifier 128 to classify sample 102 into one or more categories (e.g. pass/fail), for example by comparison with one or more classification thresholds (e.g., a high limit 126, $P_{HIGH}$, and a low limit 124, $P_{LOW}$). It will be understood by those skilled in the art that this description should be interpreted conceptually rather than literally, and that many equivalent implementations are possible.

The correction function 112, g(M), is preferably a simple function, described by a small number of parameters. Preferably, it is a linear function, a low-order polynomial (e.g., $4^{th}$-order or lower), or a parametric function, such as a Gaussian or other simple functional form, characterized by a small number of parameters (e.g., 5 parameters or less). The reference map function 118, $f(M_C)$, can, and typically will, be much more complex.

Figure 5:
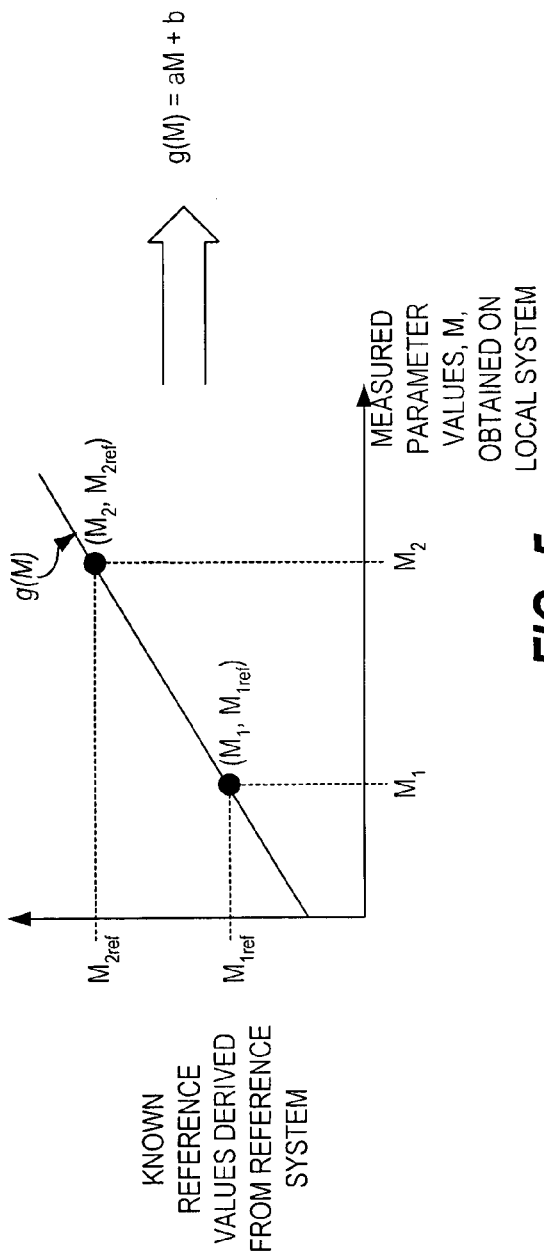
FIG. 5 is a two-dimensional graph illustrating calculation of a line function to arrive at a correction function, $g(M)$, for a system being calibrated.

FIG. 5 illustrates use of a simple linear function as a correction function, g(M), for a system being calibrated. As illustrated, measurement values, $M_1$ and $M_2$, are obtained for two calibration samples $S_1$ and $S_2$ on a local system of interest. Standard reference values, $M_{1ref}$ and $M_{2ref}$, for the same two samples are obtained either by measurement on a reference system or by simulation, as described below. Correction function g(M) is then given by:

$$M_C = M\left[\frac{M_{2ref} - M_{1ref}}{M_2 - M_1}\right] + \left[\frac{M_2 M_{1ref} - M_1 M_{2ref}}{M_2 - M_1}\right]$$

In this example, the correction function, g(M), is calculated based on only two measurements obtained on the local system, $M_1$ and $M_2$, and the corresponding reference values, $M_{1ref}$ and $M_{2ref}$, from the reference system. The corrected value, $M_C$, corresponding to any measurement, M, subsequently obtained during normal operation of the system of interest may then be found using the above equation.

The method proposed in the present invention is not restricted to linear corrections. Any low order polynomial, or other parametric function with a small number of parameters, which can be quickly and accurately fit using a small set of measured data, and which suffices to describe the differences between measurements on a pair of systems, can be used in this manner. The present invention therefore provides a means to rapidly and easily correct any two or more systems, such that they return approximately identical values of directly measured quantities.

In order to implement a complete mechanism for calibration, a reference system must be specified to which all other systems will be corrected. The reference system may be specified using various methods.

In one embodiment, a single, potentially large, reference set of calibration samples (also referred to herein as a "superset calibration test coupon") is fabricated. This reference set of calibration samples is preferably a superset of and should not be confused with the small number of calibration samples (also referred to herein as a "subset calibration test coupon") that ship with or are incorporated into each system. Careful measurements of the reference calibration samples used in the superset calibration test coupon are taken, and the results of those measurements are then used to define the reference system to which all other systems are corrected. Cost of calibration is therefore significantly reduced, since only a single copy of the superset calibration test coupon is required, rather than one per customer site. Similarly, the time required to perform extremely careful measurements of the standards is no longer problematic, since this operation is performed as little as one time on a single reference system, rather than being repeated time and again on multiple systems at multiple sites. In principle, it is even possible to destroy the reference calibration samples in order to reuse the coupon materials once the measurements are taken. However, maintenance of the reference calibration samples may be useful in establishing portability between existing system models and new system models 3D yet to be developed.

In another embodiment, detailed modeling and simulation replaces measurement to define the reference system. For an X-ray imaging system such as the Agilent 5DX, for example, Monte Carlo simulation using a coupled electron/photon transport package such as PENELOPE is appropriate. (See, F. Salvat, J. M. Fernandez-Varea, E. Acosta, and J. Semapu, "PENELOPE: A Code System for Monte Carlo Simulation of Electron and Photon transport", Issy-les-Moulineaux, France (2001) NEA/OECD). As in the case of careful measurement, differences between simulation and measurement are found to be small, so linear corrections suffice. Using simulation instead of measurement avoids difficulties and costs associated with the fabrication of reference calibration samples. For example, it may allow extending the calibration to regimes in which fabrication of accurate calibration samples is impractical. Conversely, simulation may not be a completely faithful representation of reality. The resulting systematic errors can degrade accuracy. As a result, simulation is most appropriate for inspection and classification systems where repeatability and portability are more important than accuracy.

Finally, consider construction of the reference map function, $f(M_C)$, relating a corrected measurement, $M_C$, to the physical parameter of interest, $P_e$. The invention does not simplify this relationship, which, as described above, is often complex and non-linear. The invention is advantageous over the prior art in this regard, however, in that this construction, like measurement or simulation of the standard, needs to be performed only once rather than repeated periodically on each system. As a result, considerably greater resources (e.g., time, equipment, algorithm complexity, etc.) may often be invested in the fitting procedure that generates the reference map function, $f(M_C)$, typically resulting in models more accurately reflecting the underlying relationship.

Figure 6:
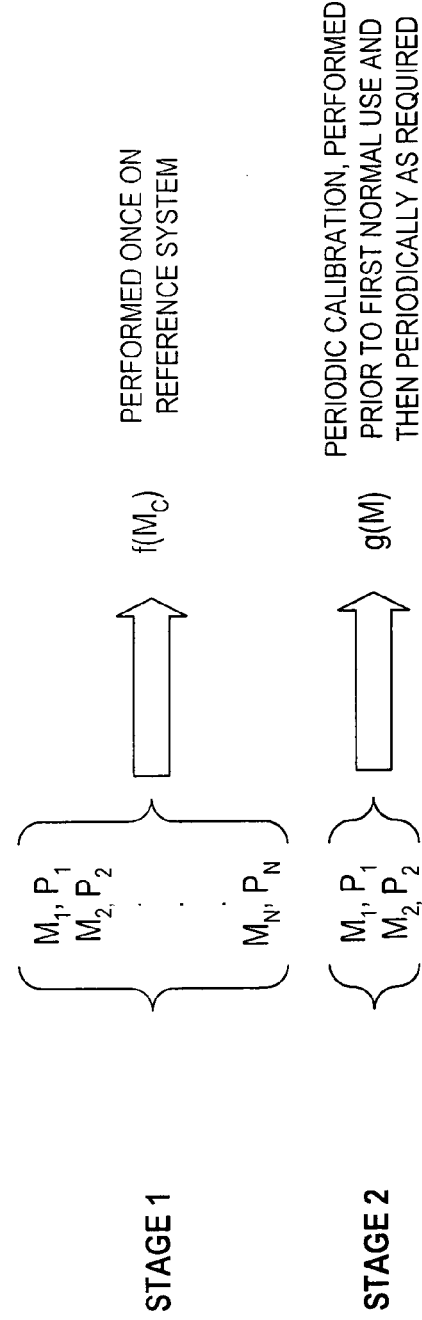
FIG. 6 is a diagram illustrating generation of a reference map function and a correction function required for two-stage calibration in accordance with the invention.
Figure 7:
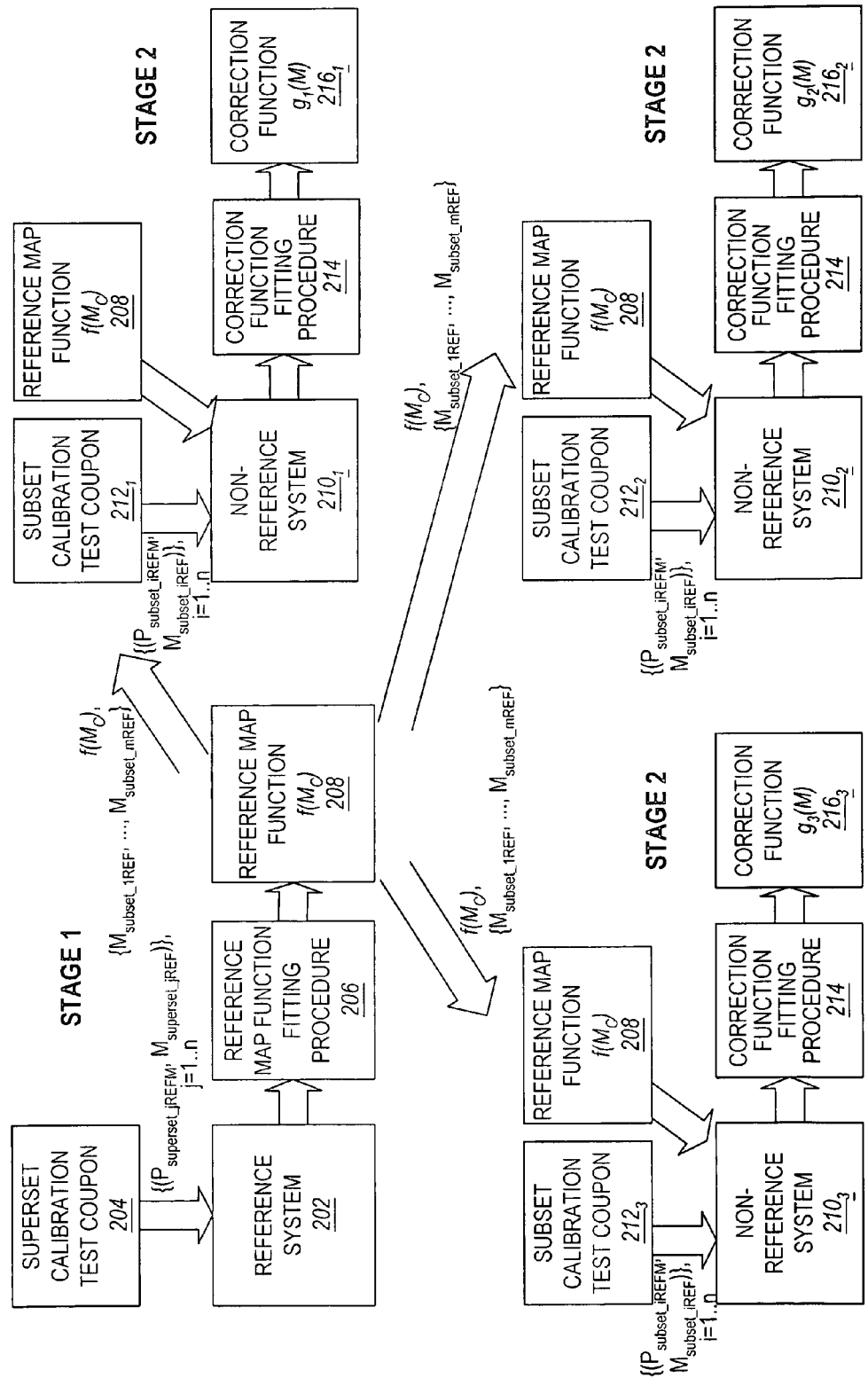
FIG. 7 is a block diagram of a plurality of indirect measurement systems illustrating the two-stage calibration process of the invention.

Calibration of an indirect measurement system is a two-stage process, as shown in FIGS. 6 and 7. As illustrated in these figures, generation of the reference map function $f(M_C)$ is performed as little as one time on a single reference system 202, while the preferably less complicated generation of the correction function g(M) is performed periodically on each system in the field (here illustrated by non-reference systems $210_1$–$210_3$), as required.

FIG. 7 illustrates application of the present invention to correct a plurality of non-reference indirect measurement systems, $210_1$, $210_2$, and $210_3$, based on a reference indirect measurement system, 202. While only three non-reference systems in addition to the reference system are shown in FIG. 7, the method is applicable to an arbitrary number of systems. As illustrated, reference map calibration is performed on the reference system 202 using a superset calibration test coupon 204 that includes a number n of calibration samples with corresponding known values $\{P_{superset\_jREF}\}$ of the physical property of interest, where j=1 to n. A reference map function fitting procedure 206 fits the known values of the physical property of interest $\{P_{superset\_jREF}\}$ to the corresponding reference values $\{M_{superset\_jREF}\}$ measured on reference system 202, to generate or estimate a reference map function 208, $f(M_C)$. Reference map calibration is the complex portion of the calibration, and the estimation of the reference map function 208, $f(M_C)$, by the map function fitting procedure 206 corresponds closely to conventional calibration of an indirect measurement system. However, it differs in that estimation of the reference map function 208, $f(M_C)$, by the map function fitting procedure 206 is performed only once on the reference system 202. This reference map function 208, $f(M_C)$, is then utilized for all other systems, $210_1$, $210_2$, and $210_3$, referred to herein as "non-reference indirect measurement systems".

Non-reference indirect measurement systems $210_1$ $210_2$, and $210_3$ are shipped with (or otherwise obtain) the reference map function 208, a correction function fitting procedure 214, and respective subset calibration test coupons, $212_1$, $212_2$, and $212_3$. Preferably, non-reference indirect measurement systems $210_1$ $210_2$, and $210_3$ are also shipped with reference values $\{M_{subset\_iREF}\}$, i=1 to m, expected for measurements on the subset coupon. Thus, in the linear calibration example of FIG. 5, as few as 2 reference values, $M_{subset\_1REF}$, $M_{subset\_2REF}$ could be provided to the non-reference indirect measurement systems $210_1$ $210_2$, and $210_3$. In the alternative, as described hereinafter, the reference values supplied may be computed by extrapolation or interpolation if the components on the subset coupon are not also found on the superset coupon.

It should further be noted that the number of subset calibration samples may even be as few as one sample. In this case, the correction function fitting procedure would be as simple as finding an additive correction (i.e., an offset) to fit the measured value to the known reference value of the sample.

Correction function calibration of each system $210_1$ $210_2$, and $210_3$ is respectively performed prior to first normal use and periodically thereafter as required to generate respective correction functions, $216_1$, $216_2$, and $216_3$ specific to the corresponding system to bring the measurements obtained on the respective systems, $210_1$, $210_2$, and $210_3$ into agreement with those which would have been obtained on reference system 202 given the same samples. To accomplish this, a reduced set of samples comprising the respective subset calibration test coupons, $212_1$, $212_2$, and $212_3$ are measured by the respective systems, $210_1$, $210_2$, and $210_3$ and fitted by the respective correction function fitting procedure 214 to generate respective correction functions, $216_1$, $216_2$, and $216_3$ specific to their respective systems $210_1$ $210_2$, and $210_3$.

As just described, the periodic correction function calibration therefore consists of conducting a greatly reduced number of measurements and fitting the measurements to construct a simple correction function, g(M). When it suffices to implement the correction function, g(M), using a linear function, for example, the reduced measurement set can consist of as few as a pair of data points, as illustrated in FIG. 5. By comparing measurements obtained on these samples to the corresponding measurements on the reference system, the correction function g(M) can be uniquely defined for a given system. Typically the samples utilized for periodic correction function calibration will be a subset of the larger group utilized for estimation of reference function $f(M_C)$, although this is not strictly required. When the periodic calibration samples are not a subset of the larger set of calibration samples used to generate the reference map function, $f(M_C)$, on the reference system, interpolation or extrapolation in $f^{-1}(P)$ can be used to identify behavior of the reference system at the measured points.

In summary, the fact that the measurement errors between indirect measuring systems are typically small is utilized in the present invention to provide an improved two-stage calibration technique. The improved technique reduces system cost, while improving portability and system availability. When required, accuracy may also be improved, since the complex portion of the calibration need be performed only once under laboratory conditions.

Turning now to a specific illustrative embodiment, the invention will be described in the context of an Automated X-ray Inspection (AXI) System, for example, the Agilent 5DX AXI System, manufactured by Agilent Technologies, Inc., of Palo Alto, Calif. In this illustrative embodiment, the parameter of interest, P, is the thickness, t, of solder, and the sensed or measured value, M, is an image gray level or X-ray intensity level.

While the following description is presented in terms of a two component assembly or portion of an assembly comprising a layer of solder and a layer of copper, it is to be understood that the present invention also applies to any two component assembly or portion of an assembly. It is to be further understood that the present invention applies equally to assemblies with three or more components. For example, when the third component is present and unchanging (e.g., the G10 substrate of a printed circuit assembly, its effect is simply to alter the effective source intensity spectrum. As such, it is not explicitly treated in the following description. The invention may also be extended to systems characterized by three or more variable components as well. Furthermore, the two components need not be in distinct layers but may be intermixed. One skilled in the art will recognize that the terms "gray level" and "intensity", as used throughout, are closely related. "Gray level" refers to a numeric value assigned to represent the brightness (or darkness) of a pixel in an image. Gray levels can be scaled arbitrarily, but a range of 0 to 255 is common. Similarly "intensity" as used in this example refers to energy per unit area or brightness of the X-ray beam. Modern X-ray imaging systems respond predictably and often linearly to given X-ray intensity. A specific image gray level is therefore functionally related to a corresponding X-ray intensity. While the two quantities are related, typically in a known way, they should not be considered identical, however.

Figures 8, 9:
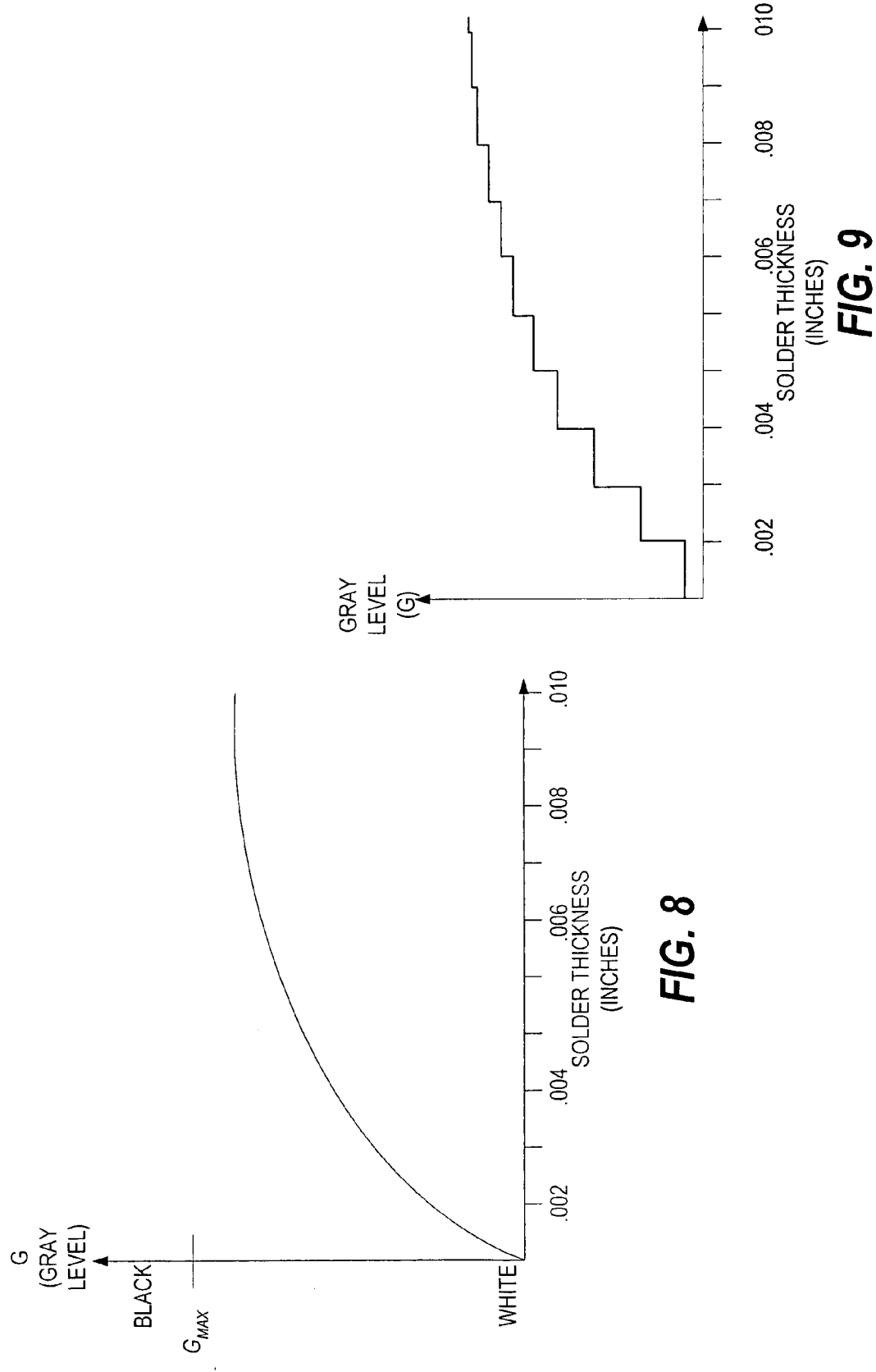
FIG. 8 is a graphical plot illustrating the relationship between solder thickness versus gray level in an image.
FIG. 9 is a graphical plot illustrating steps of solder thickness used in calibration samples and their corresponding expected gray level values.

In an X-ray image of solder material, typically a combination of lead and tin, a relationship exists between X-ray intensity or gray value and the thicknesses of the solder imaged. FIG. 8 illustrates an example of this general relationship. In this example, it is seen that the image of a thin section of solder will have a gray level that is less than the gray level of the image of a thicker section of solder, i.e. the image of the thin section will appear to be a lighter shade of gray than the image of the thicker section. This presumes an imaging system such as the 5DX which presents X-ray images as positive rather than negative. Additionally, in the following description, the gray scale ranges from zero to a maximum value $G_{MAX}$, with lower values correspond to lighter pixels and higher X-ray intensity, while values near the maximum value correspond to darker shades of gray and lower X-ray intensity. It is to be understood that other conventions for representing the gray scale may also be used. For example, lower values may be selected to correspond to the darker shades of gray (black) and the values near the maximum value may be selected to correspond to lighter shades of gray (white).

The relationship between solder thickness, t, and image gray level, G, may be calibrated using multiple but differing values of solder thickness. For illustrative purposes, FIG. 9 is a graph illustrating the relationship between gray value and solder thickness, with thicknesses ranging from 0.001 inch to 0.010 inch in increments of 0.001 inch. Since the solder thickness, t, at each of the steps is known, the corresponding gray level values, G, may be compared to the gray level values, G, of other X-ray images of solder material where the thickness values, t, are not known in order to determine the unknown thickness values, t.

In the case of circuit board assemblies, the solder is attached to a circuit board. Thus, gray scales displayed in the X-ray images include contributions from the solder as well as from the material comprising the circuit board. Typically the circuit board substrate is a plastic or resin type material and may further include ground planes and circuit traces made of a conducting material such as copper. In these cases, determination of the solder thickness is complicated by the presence of the circuit board and associated materials which contribute to background shading in the X-ray images. Background shading correction techniques for removing or minimizing the effects of such shading are described below.

Figure 10:
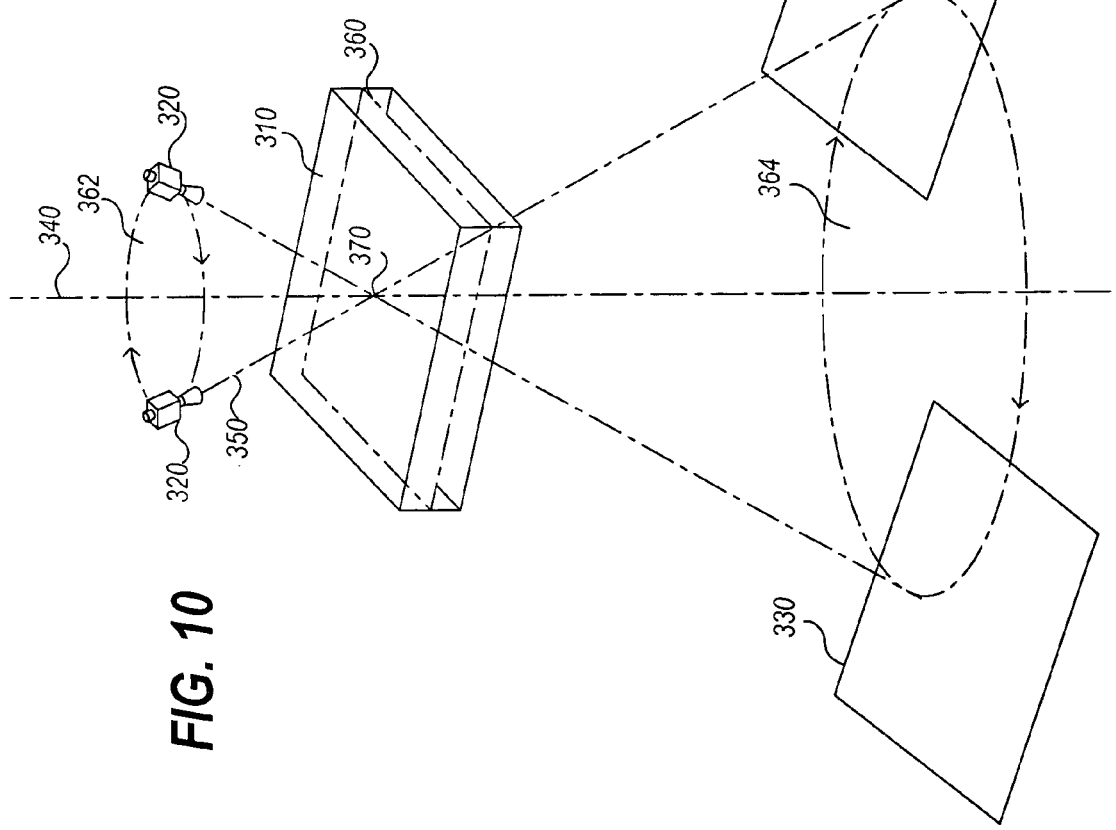
FIG. 10 is a schematic geometrical representation of a laminographic system to which the present invention may be applied.

FIG. 10 shows a schematic representation 300 of a typical laminographic geometry which may be used with the present invention. An object 310 under examination, for example, a circuit board, is held in a stationary position with respect to a source of X-rays 320 and an X-ray detector 330. Synchronous rotation of the X-ray source 320 and detector 330 about a common axis 340 causes an X-ray image of the plane 360 within the object 310 to be formed on the detector 330. The image plane 360 is substantially parallel to the planes 362 and 364 defined by the rotation of the source 320 and detector 330, respectively. The image plane 360 is located at the intersection 370 of a central ray 350 from the X-ray source 320 and the common axis of rotation 340. This point of intersection 370 acts as a fulcrum for the central ray 350, thus causing an in-focus cross-sectional X-ray image of the object 310 at the plane 360 to be formed on detector 330 as the source and detector synchronously rotate about the intersection point 370. Structure within the object 310 which lies outside of plane 360 forms a blurred X-ray image on detector 330.

In the laminographic geometry shown in FIG. 10, the axis of rotation of the radiation source 320 and the axis of rotation of the detector 330 are coaxial. However, it is not necessary that these axes of rotation of the radiation source 320 and the detector 330 be coaxial. The conditions of laminography are satisfied and a cross-sectional image of the layer 360 will be produced as long as the planes of rotation 362 and 364 are mutually parallel, and the axes of rotation of the source 320 and the detector 330 are mutually parallel and fixed in relationship to each other. It is to be understood that the present invention is not limited to any specific laminographic configuration. One skilled in the art will recognize that there are numerous alternative configurations for generating laminographic images which may also be used. Furthermore, the present invention is not limited to cross-sectional images of a two component assembly, but may be practiced with any type of X-ray image of the assembly, including but not limited to laminographic images, CT images, shadowgraph images, etc.

FIGS. 11A–11E show laminographs produced by the above described laminographic technique. The object 310 shown in FIG. 11A has test patterns in the shape of an arrow 381, a circle 382 and cross 383 embedded within the object 310 in three different planes 360a, 360b and 360c, respectively.

Figure 11A:
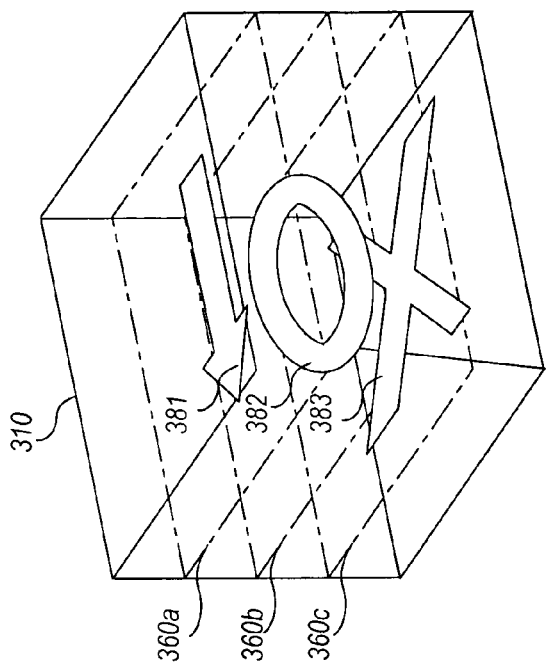
FIG. 11A is a perspective view of an object having test patterns including an arrow, a circle, and a cross embedded in three different planes of the object.
Figure 11C:
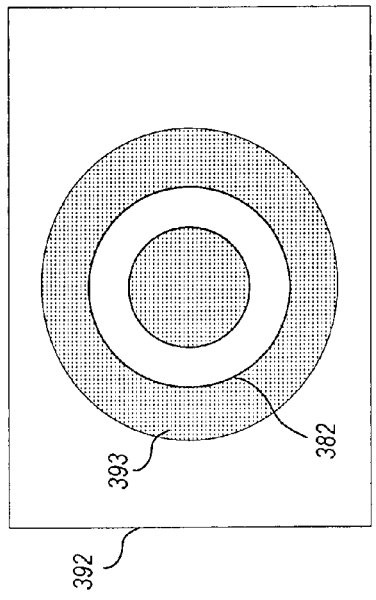
FIG. 11C is a laminograph of the object of FIG. 11A when the focal point intersects the plane comprising the circle.
Figure 11E:
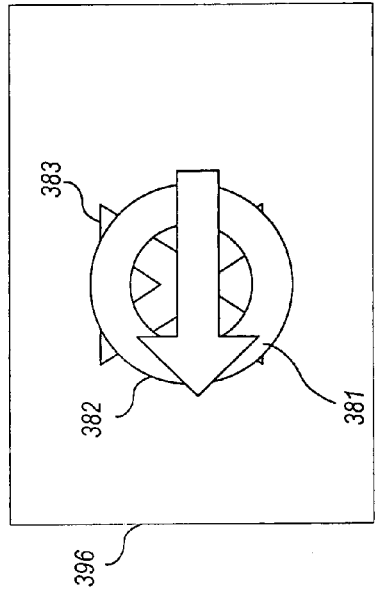
FIG. 11E is a conventional projection radiograph of the object of FIG. 11A that produces a sharp image of each of the arrow, circle, and cross in the respective planes of the object.
Figure 11B:
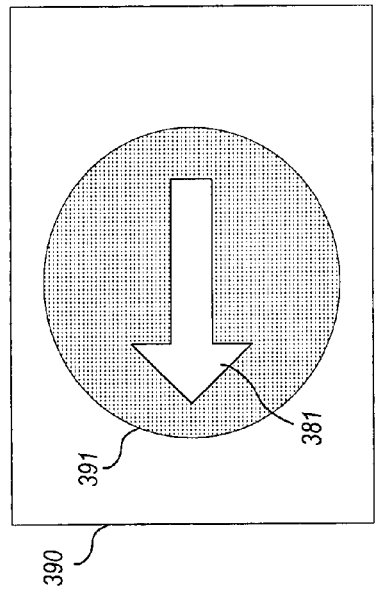
FIG. 11B is a laminograph of the object of FIG. 11A when the focal point intersects the plane comprising the arrow.

FIG. 11B shows a typical laminograph of object 310 formed on detector 330 when the point of intersection 370 lies in plane 360a of FIG. 11A. The image 390 of arrow 381 is in sharp focus, while the images of other features within the object 310, such as the circle 382 and cross 383 form a blurred region 391 which does not greatly obscure the arrow image 390.

Figure 11D:
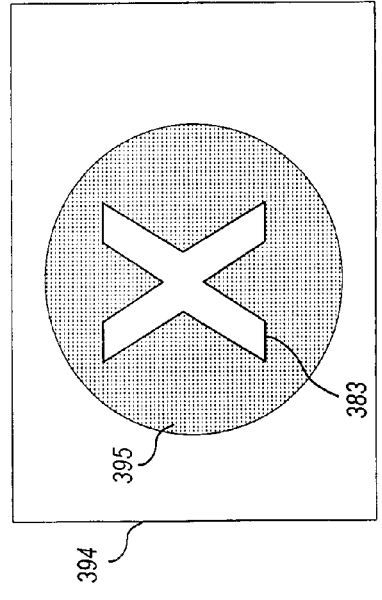
FIG. 11D is a laminograph of the object of FIG. 11A when the focal point intersects the plane comprising the cross.

Similarly, when the point of intersection 370 lies in plane 360b, the image 392 of the circle 382 is in sharp focus as seen in FIG. 11C. The arrow 381 and cross 383 form a blurred region 393. FIG. 11D shows a sharp image 394 formed of the cross 383 when the point of intersection 370 lies in plane 360c. The arrow 381 and circle 382 form blurred region 395.

For comparison, FIG. 11E shows an X-ray shadow image 396 of object 310 formed by conventional projection radiography techniques. This technique produces a sharp image of each of the arrow 381, circle 382 and cross 383, respectively, which overlap one another. FIG. 11E vividly illustrates how multiple characteristics contained within the object 310 may create multiple overshadowing features in the X-ray image which obscure individual features of the image.

FIG. 12A illustrates a schematic diagram of a typical laminographic apparatus 400 usable with the present invention. In this configuration, an object under inspection is a printed circuit board 410 having multiple electronic components 412 mounted on the board 410 and electrically interconnected via electrical connections 414 (See FIG. 12B). Typically, the electrical connections 414 are formed of eutectic solder. However, various other techniques for making the electrical connections 414 are well known in the art and even though the invention will be described in terms of solder joints, it will be understood that other types of electrical connections 414 including, but not limited to, conductive epoxy, mechanical, and non-eutectic bonds may be inspected utilizing the invention. FIG. 12B, which is a top view enlargement of a region 483 of the circuit board 410, more clearly shows the components 412 and solder joints 414, which in the illustrative embodiment are ball grid array joints.

The laminographic apparatus acquires cross-sectional images of the solder joints 414 using the previously described laminographic method or other methods capable of producing equivalent cross-sectional images. The cross-sectional images of the solder joints 414 are automatically evaluated to determine their quality and physical characteristics, including, for example, solder thickness, t. Based on the evaluation, a report of the solder joint quality and physical characteristics is presented to the user.

The laminographic apparatus, as shown in FIG. 12A, comprises an X-ray tube 402 which is positioned adjacent printed circuit assembly 410. Printed circuit assembly 410 is optionally supported by a fixture 420. Printed circuit assembly 410 or fixture 420, if present, is attached to a positioning table 430 which is capable of moving the fixture 420 and board 410 along three mutually perpendicular axes, X, Y and Z. A rotating X-ray detector 440 comprising a fluorescent screen 450, a first mirror 452, a second mirror 454 and a turntable 456 is positioned adjacent the circuit board 410 on the side opposite the X-ray tube 402. A camera 458 is positioned opposite mirror 452 for viewing images reflected into the mirrors 452, 454 from fluorescent screen 450. A feedback system 460 has an input connection 462 from a sensor 463 which detects the angular position of the turntable 456 and an output connection 464 to X and Y deflection coils 481 on X-ray tube 402. A position encoder 465 is attached to turntable 456. The position sensor 463 is mounted adjacent encoder 465 in a fixed position relative to the axis of rotation 440. The camera 458 is connected to a computer 470 via an input line 476. The computer 470 includes the capability to perform high speed image analysis. An output line 478 from the computer 470 connects the computer to positioning table 430.

The master computer 470 is connected to access a memory 496 that stores software routines in the form of program instructions, parameters, and data. In the illustrative embodiment, correction function 498 and reference map function 499 may be stored in memory 496 as procedures executed by a computer processor for computing the respective functions, as lookup tables, as parametric or non-parametric function representations, or in any other convenient form.

Figure 12C:
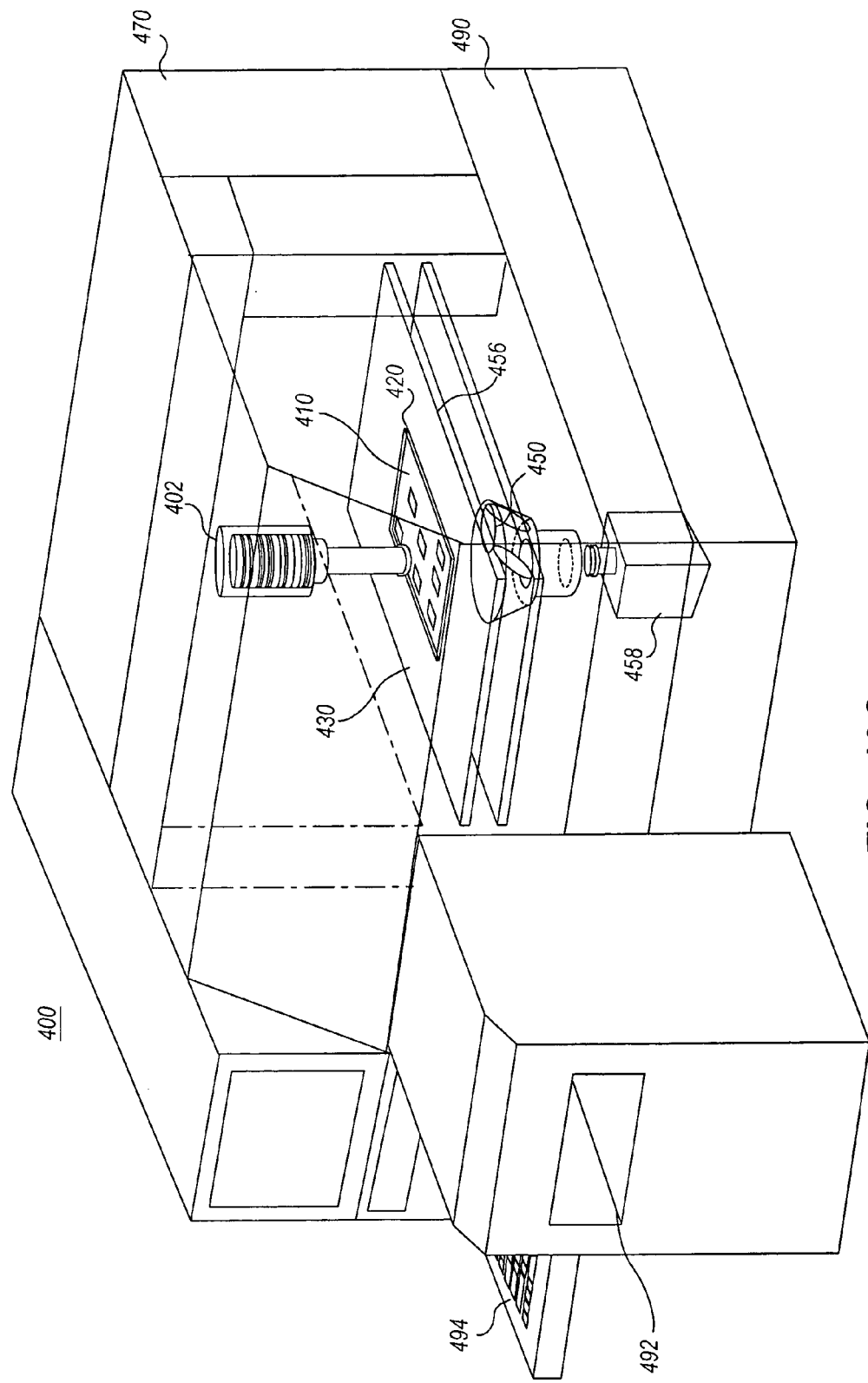
FIG. 12C is a perspective view of the embodiment of the laminographic apparatus of FIG. 12A.

A perspective view of the laminographic apparatus is shown in FIG. 12C. In addition to the X-ray tube 402, circuit board 410, fluorescent screen 450, turntable 456, camera 458, positioning table 430 and computer 470 shown in FIG. 12A, a granite support table 490, a load/unload port 492 and an operator station 494 are shown. The granite table 490 provides a rigid, vibration free platform for structurally integrating the major functional elements of the laminographic apparatus, including but not limited to the X-ray tube 402, positioning table 430 and turntable 456. The load/unload port 492 provides a means for inserting and removing circuit boards 410 from the machine. The operator station 494 provides an input/output capability for controlling the functions of the laminographic apparatus as well as for communication of inspection data to an operator.

In operation of the laminographic apparatus as shown in FIGS. 12A and 12C, high resolution, cross-sectional X-ray images of the solder joints 414 connecting components 412 on circuit board 410 are acquired using the X-ray laminographic method previously described in reference to FIGS. 10 and 11A–11E. Specifically, X-ray tube 402, as shown in FIG. 12A, comprises a rotating electron beam spot 485 which produces a rotating source 480 of X-rays 482. The X-ray beam 482 illuminates a region 483 of circuit board 410 including the solder joints 414 located within region 483. X-rays 484 which penetrate the solder joints 414, components 412 and board 410 are intercepted by the rotating fluorescent screen 450.

Dynamic alignment of the position of the X-ray source 480 with the position of rotating X-ray detector 440 is precisely controlled by feedback system 460. The feedback system correlates the position of the rotating turntable 456 with calibrated X and Y deflection values stored in a look-up table (LUT). Drive signals proportional to the calibrated X and Y deflection values are transmitted to the steering coils 481 on the X-ray tube 402. In response to these drive signals, steering coils 481 deflect electron beam 485 to locations on a target anode 487 such that the position of the X-ray source spot 480 rotates in synchronization with the rotation of detector 440 in the manner previously discussed in connection with FIG. 10.

X-rays 484 which penetrate the board 410 and strike fluorescent screen 450 are converted to visible light 486, thus creating a visible image of a single plane within the region 483 of the circuit board 410. The visible light 486 is reflected by mirrors 452 and 454 into camera 458. Camera 458 typically comprises a low light level closed circuit TV (CCTV) camera which transmits electronic video signals corresponding to the X-ray and visible images to the computer 470 via line 476.

The computer 470 sends measurement values 493, M, to the correction function 498, g(M), in memory 496 which returns corresponding corrected measurement values $M_C$ 494. The corrected measurement values 494, $M_C$, are submitted to the reference map function 499, $f(M_C)$ in memory, which returns corresponding estimated solder thickness values 495, $t_e$. A classification function, 497, determines whether to pass or fail the corresponding solder joint(s). In the simplest form of classifier, classification consists simply of comparing estimated thickness values 495, $t_e$, to upper and lower threshold limits stored in memory (not shown).

Computer 470 includes one or more processors, one or more memories and various input and output devices including but not limited to monitors, disk drives, printers and keyboards. It is to be understood that the image analysis methods of the present invention including the correction function 498 and reference map function 499 may be implemented in a variety of ways by one skilled the art. Additionally, it is to be understood that the term "image" is not limited to formats which may be viewed visually, but may also include digital or analog representations which may be acquired, stored and analyzed by the computer.

Computer 470 also controls the movement of positioning table 430 and thus circuit board 410 so that different regions of circuit board 410 containing solder joints of interest may be automatically positioned within inspection region 483.

Figures 14A, 14B, 14C:
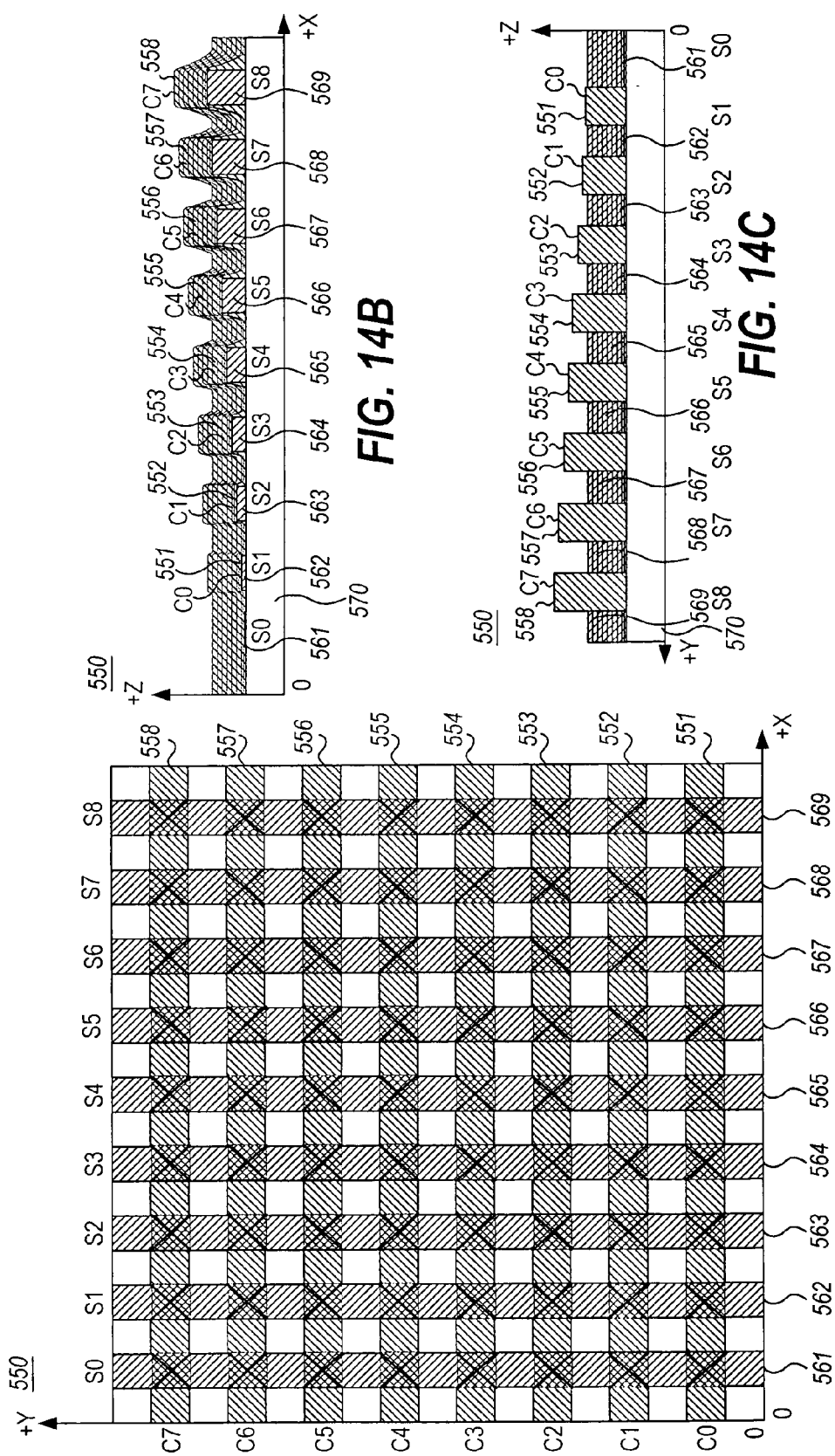
FIG. 14A is a top view (in the x-y dimension) of a superset calibration test coupon used for calibrating a reference laminographic apparatus such as that of FIG. 12A to generate a reference map function $f(M_C)$.
FIG. 14B is a side view (in the x-z dimension) of the superset calibration test coupon of FIG. 14A.
FIG. 14C is a side view (in the y-z dimension) of the superset calibration test coupon of FIGS. 14A and 14B.

FIG. 13 shows a schematic cross sectional representation of a portion of a two component assembly 500 comprising a first material 510 (e.g., solder) in combination with a second material 520 (e.g., copper, plastic, etc). As shown in FIG. 13, X-rays 530 having a incident intensity $I_0$, are directed upon the assembly 500 from a first side and encounter regions of the assembly 500 which include the first material 510 having a thickness $t_1$ in combination with the second material 520 having a thickness $t_2$, and other regions of the assembly 500 which include only the second material 520. In regions where the X-rays have passed through only the second material 520, the incident intensity $I_0$ is attenuated to an intensity $I_1$. Similarly, in regions where the X-rays have passed through both the first material 510 and the second material 520, the incident intensity $I_0$ is attenuated to an intensity $I_2$. Ignoring scattering, the absorption of monochromatic X-rays in the region including only the second material 520 is governed by the following relation:

$$I_1 = I_0 e^{(-\alpha_2 t_2)}$$

where $\alpha_2$ is the linear X-ray attenuation coefficient for the second material 520. The absorption of monochromatic X-rays in the region including both the first material 510 and the second material 520 is governed by the following relation:

$$I_2 = I_0 e^{(-\alpha_1 t_1)} e^{(-\alpha_2 t_2)}$$

where $\alpha_1$ is the linear X-ray attenuation coefficient for the first material 510. FIG. 13 illustrates the X-rays 530 passing through the assembly 500 in a direction which is perpendicular to the first and second layers 510 and 520, thus, $t_1$ and $t_2$ represent the thicknesses of the first and second layers 510 and 520, respectively. In the event the X-rays pass through the assembly at some other angle, $t_1$ and $t_2$ represent the distances the X-rays have traveled through the first and second layers 510 and 520, respectively. FIGS. 14A–14C respectively illustrate a top view (in the x-y dimension), a side view (in the x-z dimension), and a side view (in the y-z dimension) of a superset calibration test coupon 550 used in calibrating a reference AXI system to generate the reference map function $f(M_C)$. The superset calibration test coupon comprises eight copper strips 551, 552, 553, 554, 555, 556, 557, 558 of varying thickness (C0, C1, C2, C3, C4, 5, C6, and C7, where C0 is a minimum thickness (which may even include zero thickness) and C7 is a maximum thickness) intersecting nine solder strips 561, 562, 563, 564, 565, 566, 567, 568, 569 of varying thickness (S0, S1, S2, S3, S4, S5, S6, S7, and S8, where S0 is a minimum thickness (which may even include zero thickness) and S8 is a maximum thickness), for a total of seventy-two intersections which comprise the "representative" calibration samples. The strips are assembled into a printed circuit board assembly comprised of materials 570 widely used in printed circuit boards (e.g., a G10 substrate).

Various methods exist for implementing the reference map function fitting procedure 472, and will of course depend on the particular subject application or measurement system. In the case of the Agilent 5DX AXI System, the fitting procedure for generating $f(M_C)$ is preferably performed according to one or more of several fitting procedure embodiments described in U.S. Pat. No. 6,201,850 (incorporated herein by reference for all that it teaches) to Heumann and owned by the assignee of interest. Generally, the fitting procedure 472 involves a non-linear shading correction technique based on the assumptions that 1) plots of delta gray level (y=ΔG, the difference between foreground and background gray levels) at particular solder thickness on the y-axis vs. background gray level on the x-axis may be approximated by points located on a left branch of a series of hyperbolic curves having two common parameters including a common x-axis value at which each hyperbola assumes its minimum value of y (i.e., ΔG), and a common x-axis intercept ($x=x_0$), and 2) at a "nominal" or reference background gray level, the delta gray level due to solder ($y_0$) vs. solder thickness (t), function may be approximated by a fitted curve of known form, e.g., a sum of exponentials. The procedure involves fitting multiple sets of calibration data to hyperbolic functions of the form:

$$y = \Delta G = \sqrt{(x-a)^2 + b^2} + c \qquad (3)$$

where a is the common (non-physical) x-axis value at which each hyperbola has a minimum value, and all of the hyperbolae share a common x-axis intercept at $x_0 = a - \sqrt{c^2 - b^2}$. Here, y represents the delta-gray level values, x represents the background gray level, and each hyberbola corresponds to a particular solder thickness. Once a set of calibration curves are fitted to the sample data, these curves are used as the reference map $f(M_C)$ to map measured gray values to solder thickness during normal operation of the AXI system.

Figure 15:
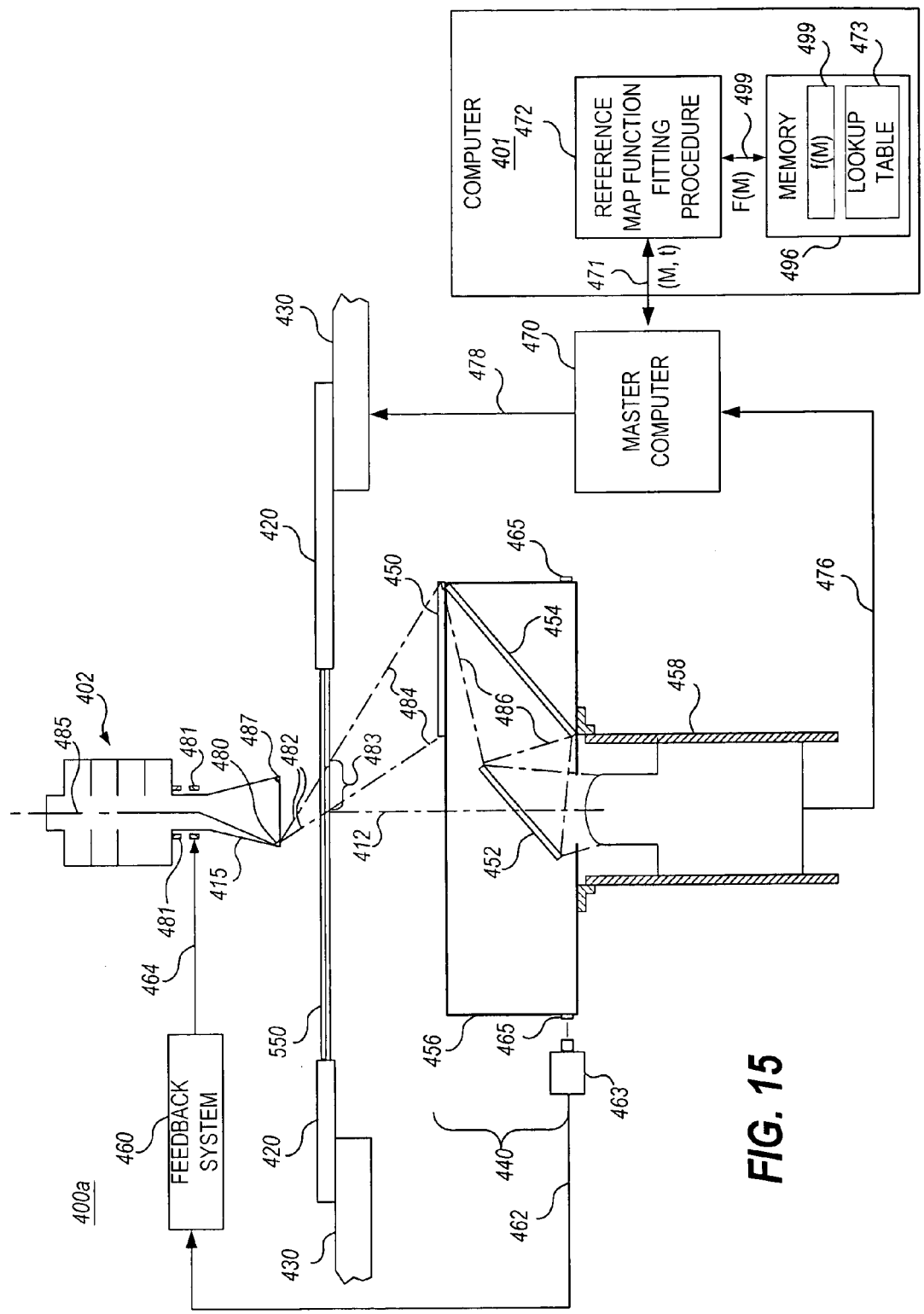
FIG. 15 is a schematic diagram of the laminographic apparatus of FIG. 12A in which the superset test calibration coupon of FIGS. 14A–14C is under inspection.

To generate the reference map function, $f(M_C)$, the superset calibration test coupon printed circuit board 550 is inserted into a reference AXI system 400a, as illustrated in FIG. 15, which measures the gray values of X-ray images of each intersection (marked with an "x" on the test coupon 550) under standard conditions. The reference AXI system 400a is a system such as the system 400 of FIG. 12A that is designated as the reference to which all other identical-by-design systems will be calibrated. Accordingly, in FIG. 15, all identical components are shown with the same reference signs as those shown in FIG. 12A. A reference map function fitting procedure 472, executing on a remote computer system 401, generates a mathematical model, i.e., the reference map function $f(M_C)$, describing the non-linear relation between gray value measured on the reference system, M, and known solder thickness, t.

In the alternative, as discussed previously, detailed modeling and simulation may replace obtaining superset calibration test coupon sample measurements to define the reference system, for example, using the PENELOPE Monte Carlo simulation package described previously.

Once a reference map function 499, $f(M_C)$, is generated, it may be stored in the AXI system memory 496 as either a software routine comprising programmable instructions for execution by the AXI system hardware, as a lookup table 473 comprising pairs of gray values and corresponding solder thicknesses, $\{M_i, t_i\}$, where i=1 to N, as a parametric or non-parametric function representation, or in any convenient form. When the reference map function 499, $f(M_C)$, is complex, as it typically will be in AXI systems, it will often be preferable to generate a lookup table 473 which may be accessed and interpolated more efficiently than $f(M_C)$ can be computed.

As discussed previously, once initially calibrated, an AXI system should be periodically recalibrated (i.e., correction function calibration should be performed) to ensure portability and accuracy. However, as also previously discussed, recalibration using a reference superset test coupon 550 and the fitting procedure 472 just described is a time-consuming and costly process. Accordingly, the present invention introduces a simplified correction calibration procedure for calibration any time after the initial factory calibration.

In the illustrative embodiment, the correction function fitting procedure involves the use of a simplified test coupon, for example a two-point test coupon 580 illustrated in FIGS. 16A, 16B, and 16C, and a linear calculation function 498 for generating correction function g(M) that calculates a straight line function using measurement data from each of the two samples or intersection points (marked with an "x" on the coupon.

As shown in FIGS. 16A, 16B, and 16C, the two-point test coupon 580 comprises two copper rectangles, dots, or other shapes, 581a, 581b, of predefined thickness (e.g., C7) overlaid by two corresponding solder rectangles, dots, or other shapes 582a, 582b, of varying thicknesses (e.g., S0 and S9), for a total of two "representative" calibration samples (located at the two intersections marked with an "x" in FIG. 16A). Preferably, the thickness of the two solder samples 582a, 582b are widely separated, spanning the desired operating range of the systems to be calibrated, where one may even have zero thickness. The copper/solder samples 581a/582a, 581b/582b are assembled into a printed circuit board assembly 580 comprised of materials 584 widely used in printed circuit boards (e.g., a G10 substrate).

The correction function fitting procedure 492 that generates the correction function 498, g(M), can simply determine the equation of the line mapping the first and second measured values to the corresponding reference values. The correction function fitting procedure 492 can be implemented either as a software routine residing in system memory 496 comprising program instructions executed by the master computer 470 or as a software routine comprising program instructions residing in the memory of a remote computer 403, or may be implemented in hardware. Preferably, since only two well-separated points are required, thicknesses can be chosen to minimize the difficulties in production of the calibration samples. For example, one can choose to use air (zero thickness) as one sample, and thick copper plus thick solder as the other sample. Measured gray values at high thickness are relatively insensitive to minor changes in thickness. Additional data points, if implemented on the subset calibration test coupon, can be used to assign confidence intervals to the parameters of the fitted line. It has been found that a simple, linear correction such as that just described, accounts for greater than 99.5% of the variation between Agilent 5DX systems, despite the fact that these are large, complex systems. Thus, by measuring only two calibration samples, rather than the large number used in the superset calibration test coupon to determine the reference map function $f(M_C)$, such systems can be brought into excellent agreement with each other more quickly, more economically, and sometimes more accurately than with conventional calibration methods.

As stated previously, the method proposed in the present invention is not restricted linear corrections. Any low order polynomial, or other parametric function with a small number of parameters, which can be quickly and accurately fit using a small set of measured data, and which suffices to describe the differences between measurements on a pair of systems, can be used in this manner.

To generate the correction function, g(M), the subset calibration test coupon printed circuit board 580 is inserted into a local AXI system 400b (which is generally a different system from, but identical in design as, the reference AXI system 400a), as illustrated in FIG. 17, which measures the gray values of X-ray images of each of the two test points, or intersections (marked with an "x" on the test coupon 580) on the two-point test coupon 580 under standard conditions. The local AXI system 400b is a system such as the system 400 of FIG. 12A that is to be calibrated to the reference system 400a of FIG. 15. Its main functional components are identical by design to the reference system of FIG. 15; accordingly all identical components are shown with the same reference signs as those shown in FIG. 15.

The AXI system software includes a correction function fitting procedure 492, which receives the calibration sample data 491, (M, t), for each subset calibration test coupon calibration sample, and generates a correction function 498, g(M), which can take any gray level value of M and correct it to its calibrated value $M_C$. The correction function fitting procedure 492 fits the calibration sample points and associated reference values to a line to generate g(M). Because g(M) is a simple linear equation, a low order polynomial, or parametric function with a small number of parameters, the correction function 498, g(M), can be and preferably is efficiently implemented in software rather than stored as a lookup table. However, lookup table or alternative representations for g(M) can also be used.

Figure 18:
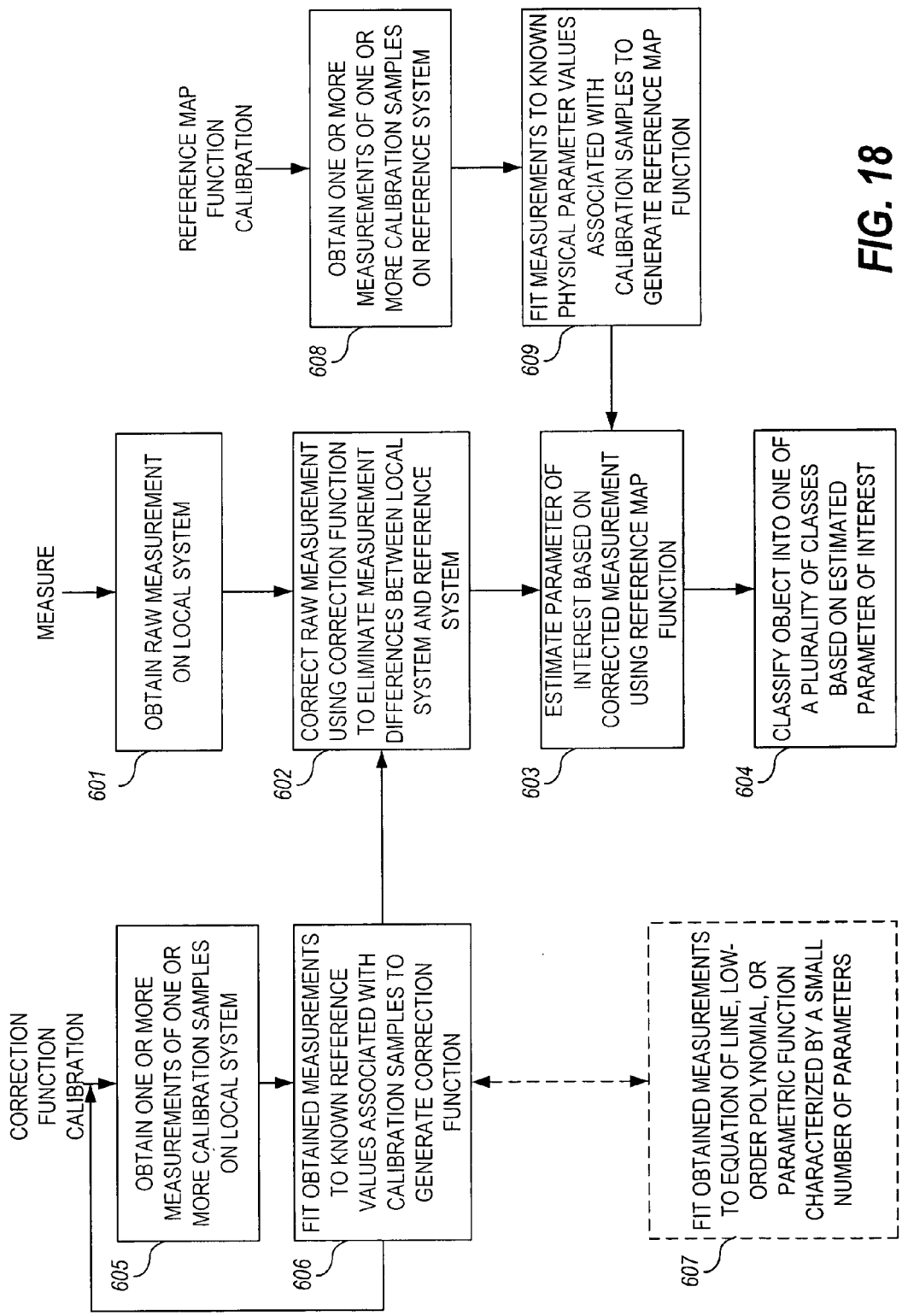
FIG. 18 is a flowchart illustrating the method of measurement and two-stage calibration of the invention.

In summary, the present invention provides a system and method for determining an estimated value of a parameter of interest of an object. FIG. 18 is a flowchart illustrating the measurement method 600 of the invention, in which a raw measurement that is indirectly representative of a parameter of interest of the object is obtained (step 601), the raw measurement is corrected to a corrected measurement to minimize measurement differences between the indirect measurement system and a reference indirect measurement system (step 602), and a value of the parameter of interest of the object is estimated based on the corrected measurement (step 603). Preferably, the physical parameter value is used to classify the object into one of a plurality of classes (step 604).

In the preferred embodiment, as discussed previously, the step for correcting the raw measurement to the corrected measurement utilizes a correction function in the form of either a linear equation, a low-order polynomial, or a parametric function characterized by a small number of parameters (such as a Gaussian or other simple functional form) (step 607) to determine the corrected measurement.

The correction function is determined (step 606) based on measurements of one or more calibration samples obtained (step 605) using the indirect measurement system and known reference values associated with each of the one or more calibration samples.

The reference map function is preferably determined (step 609) based on measurements of a plurality of calibration samples obtained (step 608) using the reference indirect measurement system and corresponding known values of the physical property of interest associated with each of said plurality of calibration samples. Although this preferred embodiment of the present invention has been disclosed for illustrative purposes, those skilled in the art will appreciate that various modifications, additions and substitutions are possible, without departing from the scope and spirit of the invention as disclosed in the accompanying claims. The laminographic geometry and apparatus shown and described with reference to FIGS. 10–12 are typical of that which may be used in conjunction with the present invention. However, specific details of these systems are not critical to the practice of the present invention, which addresses a two-stage method for calibration of indirect measurement systems in general. For example, the number of computers and delegation of tasks to specific computers may vary considerably from system to system as may the specific details of the parameter of interest, the indirect sensor mechanism, etc. The present invention is applicable to any type of system which derives a parameter of interest from an indirect measurement (i.e., by measuring a different parameter and mapping the measured parameter to the parameter of interest), and is not limited to AXI systems which have been described herein for purposes of illustration. It is also possible that other benefits or uses of the currently disclosed invention will become apparent over time.

What is claimed is:

1. An indirect measurement system for determining an estimated value of a parameter of interest of an object, comprising:
    a sensor that produces a raw measurement that is indirectly representative of said parameter of interest of said object;
    a correction function processor which performs a correction function that corrects said raw measurement to a corrected measurement to minimize measurement differences between said indirect measurement system and a reference indirect measurement system;
    a reference map function processor which performs a reference map function that estimates said estimated value of said parameter of interest of said object based on said corrected measurement; and
    a correction function fitting procedure processor which performs a correction function fitting procedure that fits said correction function based on reference values for one or more calibration samples measured on or simulated for said reference indirect measurement system and corresponding values measured on said indirect measurement system.

2. An indirect measurement system in accordance with claim 1, wherein:
    said correction function comprises one of a low-order polynomial function and a parametric function characterized by a small number of parameters.

3. An indirect measurement system in accordance with claim 1, comprising:
    a reference map function fitting procedure processor whith performs a reference map function fitting procedure that fits said reference map function based on known values of the parameter of interest associated with each of one or more reference calibration samples and corresponding reference values for said one or more reference calibration samples measured on or simulated for said reference indirect measurement system.

4. An indirect measurement system in accordance with claim 1, comprising:
    a classification function that classifies said object into one of a plurality of classes based on said estimated value of said parameter of interest.

5. A system for calibrating a first indirect measurement system with respect to a second indirect measurement system, said first indirect measurement system comprising a sensor that produces a raw measurement that is indirectly representative of a parameter of interest of an object sensed by said sensor, a correction function processor which performs a correction function that corrects said raw measurement to a corrected measurement to minimize measurement differences between said first indirect measurement system and said second indirect measurement system, and a reference map function processor which performs a reference map function that estimates an estimated value of said parameter of interest of said object based on said corrected measurement, said system comprising:
    a correction function fitting procedure processor which performs a correction function fitting procedure that fits said correction function based on reference values for one or more calibration samples measured on or simulated for said second indirect measurement system and corresponding values measured on said first indirect measurement system.

6. A system in accordance with claim 5, wherein:
    said correction function comprises one of a low-order polynomial function and a parametric function characterized by a small number of parameters.

7. A system in accordance with claim 5. wherein:
    said correction function fitting procedure permits updating said correction function without updating said reference map function.

8. A system in accordance with claim 5, comprising:
    a reference map function fitting procedure processor that fits said reference map function based on known values of the parameter of interest associated with each of one or more reference calibration samples and corresponding reference values for said one or more reference calibration samples measured on or simulated for said second indirect measurement system.

9. A method for calibrating a first indirect measurement system with respect to a second indirect measurement system, said first indirect measurement system comprising a sensor that produces a raw measurement that is indirectly representative of a parameter of interest of an object sensed by said sensor, a correction function that corrects said raw measurement to a corrected measurement to minimize measurement differences between said first indirect measurement system and said second indirect measurement system, and a reference map function that estimates an estimated value of said parameter of interest of said object based on said corrected measurement, said method comprising the steps of:
    obtaining measurement values of one or more calibration samples measured on said first indirect measurement system; and
    fitting said correction function based on said obtained measurement values of said one or more calibration samples and corresponding known reference values measured on or simulated for said second indirect measurement system.

10. A method in accordance with claim 9, wherein:
    said correction function comprises one of a row-order polynomial function and a parametric function characterized by a small number of parameters.

11. A method in accordance with claim 9, further comprising the steps of:
    re-obtaining measurement values of said one or more calibration samples measured on said first indirect measurement system; and re-fitting said correction function based on said re-obtained measurement values of said one or more calibration samples and corresponding known reference values measured on or simulated for said second indirect measurement system.

12. A method in accordance with claim 9, further comprising the steps of:
obtaining reference values of one or more reference calibration samples measured on or simulated far said second indirect measurement system; and
fitting said reference map function based on said obtained reference values of said one or more reference calibration samples to corresponding known values of the parameter of interest associated with each of said one or more reference calibration samples.

13. A method in accordance with claim 12, further comprising:
updating said correction function without updating said reference map function.

14. A computer readable storage medium tangibly embodying program instructions implementing a method for calibrating a first indirect measurement system with respect to a second indirect measurement system, said first indirect measurement system comprising a sensor that produces a raw measurement that is indirectly representative of a parameter of interest of an object sensed by said sensor, a correction function that corrects said raw measurement to a corrected measurement to minimize measurement differences between said first indirect measurement system and said second indirect measurement system, and a reference map function that estimates an estimated value of said parameter of interest of said object based on said corrected measurement, the method comprising the steps of:
obtaining measurement values of one or more calibration samples measured on said first indirect measurement system; and
fitting said correction function based on said obtained measurement values of said one or more calibration samples and corresponding known reference values measured on or simulated for said second indirect measurement system.

15. The computer readable storage medium of claim 14, wherein:
said correction function comprises one of a low-order polynomial function and a parametric function characterized by a small number of parameters.

16. The computer readable storage medium of claim 14, the method further comprising the steps of:
re-obtaining measurement values of said one or more calibration samples measured on said first indirect measurement system; and
re-fitting said correction function based on said re-obtained measurement values of said one or more calibration samples and corresponding known reference values measured on or simulated for said second indirect measurement system.

17. The computer readable storage medium of claim 14, the method further comprising the steps of:
obtaining reference values of one or more reference calibration samples measured on or simulated for said second indirect measurement system; and
fitting said reference map function based on said obtained reference values of said one or more reference calibration samples to corresponding known values of the parameter of interest associated with each of said one or more reference calibration samples.

18. The computer readable storage medium of claim 17, the method further comprising the step of:
updating said correction function without updating said reference map function.

19. An automated inspection system, comprising:
an imaging system utilizing a source of penetrating radiation and one or more sensors to detect said penetrating radiation reflected by, scattered by, transmitted through, or emitted from an object and to generate an image of said object from which is derived one or more features of said object that are representative of a parameter of interest of said object;
a correction function processor which performs a correction function that corrects said one or more features derived from said image of said object to one or more corresponding corrected features to minimize differences between said automated inspection system and a reference automated inspection system; and
a reference map function processor which performs a reference map function that estimates an estimated value of said parameter of interest of said object based on said one or more corresponding corrected features; and
a correction function fitting procedure processor which performs a correction function fitting procedure that fits said correction function based on one or more features derived from one or more images of one or more calibration samples imaged on said automated inspection system and corresponding reference features derived from one or more reference images imaged on said reference automated inspection system.

20. An automated inspection system in accordance with claim 19, wherein:
said correction function comprises one of a low-order polynomial function and a parametric function characterized by a small number of parameters.

21. An automated inspection system in accordance with claim 19, comprising:
a classification function processor that classifies said object into one of a plurality of classes based on said estimated value of said parameter of interest.

22. An automated inspection system in accordance with claim 19, wherein:
said source of penetrating radiation comprises x-rays; and
said image of said object comprises a gray level value representing detection of said x-rays.

23. An automated inspection system in accordance with claim 19, wherein:
said object comprises a solder joint of a printed circuit board and said parameter of interest is a solder thickness of said solder joint or a portion thereof.

24. A system for calibrating a first automated inspection system with respect to a second automated inspection system, said first automated inspection system comprising an imaging system utilizing a source of penetrating radiation and one or more sensors to detect said penetrating radiation reflected by, scattered by, transmitted through, or emitted from an object and to generate an image of said object from which is derived one or more features of said object that are representative of a parameter of interest of said object, a correction function processor which performs a correction function that corrects said one or more features derived from said image of said object to one or more corresponding corrected features to minimize differences between said first automated inspection system end said second automated inspection system, and a reference map function processor which performs a reference map function that estimates an estimated value of said parameter of interest of said object based on said one or more corresponding corrected features, said system comprising:
a correction function fitting procedure processor that fits said correction function based on one or more features derived from one or more images of one or more calibration samples imaged on said first automated inspection system and corresponding reference features derived from one or more reference images imaged on said second automated inspection system.

25. A system in accordance with claim 24, wherein:
said correction function comprises one of a low-order polynomial function and a parametric function characterized by a small number of parameters.

26. A system in accordance with claim 24, wherein:
said correction function fitting procedure processor updates said correction function without updating said reference map function.

27. A system in accordance with claim 24, comprising:
a reference map function fitting procedure processor that fits said reference map function based on known values of the parameter of interest associated with each of one or more reference calibration samples and corresponding reference features derived from one or more images of said one or more reference calibration samples imaged on said second automated inspection system.

28. A system in accordance with claim 24, wherein:
said source of penetrating radiation comprises x-rays; and
said image of said object comprises a gray level value representing detection of said x-rays.

29. A system in accordance with claim 24, wherein:
said object comprises a solder joint of a printed circuit board and said parameter of interest is a solder thickness of said solder joint or a portion thereof.

30. A method for calibrating a first automated inspection system with respect to a second automated inspection system, said first automated inspection system comprising an imaging system utilizing a source of penetrating radiation and one or more sensors to detect said penetrating radiation reflected by, scattered by, transmitted through, or emitted from an object and to generate an image of said object from which is derived one or more features of said object that are representative of a parameter of interest of said object, a correction function that corrects said one or more features derived from said image of said object to one or more corresponding corrected features to minimize differences between said first automated inspection system and said second automated inspection system, and a reference map function that estimates an estimated value of said parameter of interest of said object based on said one or more corresponding corrected features, said method comprising:
obtaining one or more features derived from one or more images of one or more calibration samples imaged on said first automated inspection system; and
fitting said correction function based on said one or more features derived from said one or more images of said one or more calibration samples and corresponding reference features derived from one or more reference images imaged on said second automated inspection system.

31. A method in accordance with claim 30, wherein:
said correction function comprises one of a low-order polynomial function and a parametric function characterized by a small number of parameters.

32. A method in accordance with claim 30, comprising:
re-obtaining one or more features derived from one or more images of said one or more calibration samples imaged on said first automated inspection system; and
re-fitting said re-obtained one or more features derived from said one or more images of said one or more calibration samples and corresponding reference features derived from one or more reference images imaged on or simulated for said second automated inspection system.

33. A method in accordance with claim 30, further comprising the steps of:
obtaining one or more reference features derived from one or more images of one or more reference calibration samples imaged on said second automated inspection system; and
fitting said reference map function based on said obtained one or more reference features derived from said one or more images of said one or more reference calibration samples and corresponding known values of the parameter of interest associated with each of said one or more reference calibration samples.

34. A method in accordance with claim 33, further comprising the step of updating said correction function without updating said reference map function.

35. A method in accordance with claim 30, wherein:
said source of penetrating radiation comprises x-rays; and
said one or more images or features derived therefrom comprises a gray level value reflecting detection of said x-rays penetrating said object.

36. A method in accordance with claim 30, wherein:
said object comprises a solder joint of a printed circuit board and said parameter of interest is a solder thickness of said solder joint or a portion thereof.

37. A computer readable storage medium tangibly embodying program instructions implementing a method for calibrating a first automated inspection system with respect to a second automated inspection system, said first automated inspection system comprising an imaging system utilizing a source of penetrating radiation and one or more sensors to detect said penetrating radiation reflected by, scattered by, transmitted through, or emitted from an object and to generate an image of said object from which is derived one or more features of said object that are representative of a parameter of interest of said object, a correction function that corrects said one or more features derived from said image of said object to one or more corresponding corrected features to minimize differences between said first automated inspection system and said second automated inspection system, and a reference map function that estimates an estimated value of said parameter of interest of said object based on said one or more corresponding corrected features, the method comprising the steps of:
obtaining one or more features derived from one or more images of one or more calibration samples imaged on said first automated inspection system; and
fitting said correction function based on said one or more features derived from said one or more images of said one or more calibration samples and corresponding reference features derived from one or more reference images imaged on said second automated inspection system.

38. The computer readable storage medium of claim 37, wherein:
said correction function comprises one of a low-order polynomial function and a parametric function characterized by a small number of parameters.

39. The computer readable storage medium of claim 37, the method further comprising:
  re-obtaining one or more features derived from one or more images of said one or more calibration samples imaged on said first automated inspection system; and
  re-fitting said re-obtained one or more features derived from said one or more images of said one or more calibration samples and corresponding reference features derived from one or more reference images imaged on or simulated for said second automated inspection system.

40. The computer readable storage medium of claim 37, the method further comprising:
  obtaining one or more reference features derived from one or more images of one or more reference calibration samples imaged on said second automated inspection system; and
  fitting said reference map function based on said obtained one or more reference features derived from said one or more images of said one or more reference calibration samples and corresponding known values of the parameter of interest associated with each of said one or more reference calibration samples.

41. The computer readable storage medium of claim 40, further comprising the step of:
  updating said correction function without updating said reference map function.

42. A method in accordance with claim 37, wherein:
  said source of penetrating radiation comprises x-rays; and
  said one or more images or features derived therefrom comprises a gray level value reflecting detection of said x-rays penetrating said object.

43. A method in accordance with claim 37, wherein:
  said object comprises a solder joint of a printed circuit board and said parameter of interest is a solder thickness of said solder joint or a portion thereof.

* * * * *

UNITED STATES PATENT AND TRADEMARK OFFICE
CERTIFICATE OF CORRECTION

PATENT NO. : 7,108,424 B2  Page 1 of 1
APPLICATION NO. : 10/797993
DATED : September 19, 2006
INVENTOR(S) : Heumann et al.

It is certified that error appears in the above-identified patent and that said Letters Patent is hereby corrected as shown below:

On the Title page, in item (57), under "Abstract", in column 2, line 4, delete "filling" and insert -- fitting --, therefor.

On the Title page, in item (57), under "Abstract", in column 2, line 8, delete "fining" and insert -- fitting --, therefor.

Column 19, line 55, in Claim 3, delete "whith" and insert -- which --, therefor.

Column 20, line 26, in Claim 7, delete "5." and insert -- 5, --, therefor.

Column 20, line 60, in Claim 10, delete "row" and insert -- low --, therefor.

Column 21, line 9, in Claim 12, delete "far" and insert -- for --, therefor.

Column 22, line 65, in Claim 24, delete "end" and insert -- and --, therefor.

Signed and Sealed this

Twentieth Day of March, 2007

JON W. DUDAS
*Director of the United States Patent and Trademark Office*